US010781196B2

(12) United States Patent
Saha et al.

(10) Patent No.: US 10,781,196 B2
(45) Date of Patent: Sep. 22, 2020

(54) INTEGRATED PROCESS FOR DIRECT SACCHARIFICATION AND DEHYDRATION OF INTACT BIOMASS TO FURFURALS

(71) Applicants: Basudeb Saha, Newark, DE (US); Sunitha Sadula, Newark, DE (US); Dionisios Vlachos, Voorhees, NJ (US)

(72) Inventors: Basudeb Saha, Newark, DE (US); Sunitha Sadula, Newark, DE (US); Dionisios Vlachos, Voorhees, NJ (US)

(73) Assignee: UNIVERSITY OF DELAWARE, Newark, DE (US)

(*) Notice: Subject to any disclaimer, the term of this patent is extended or adjusted under 35 U.S.C. 154(b) by 0 days.

(21) Appl. No.: 16/323,000

(22) PCT Filed: Aug. 15, 2017

(86) PCT No.: PCT/US2017/046874
§ 371 (c)(1),
(2) Date: Feb. 4, 2019

(87) PCT Pub. No.: WO2018/035083
PCT Pub. Date: Feb. 22, 2018

(65) Prior Publication Data
US 2019/0161463 A1    May 30, 2019

Related U.S. Application Data

(60) Provisional application No. 62/375,991, filed on Aug. 17, 2016.

(51) Int. Cl.
*C07D 307/50* (2006.01)
*C13K 1/02* (2006.01)
*C13K 13/00* (2006.01)
*C08H 8/00* (2010.01)

(52) U.S. Cl.
CPC ............. *C07D 307/50* (2013.01); *C08H 8/00* (2013.01); *C13K 1/02* (2013.01); *C13K 13/002* (2013.01); *Y02P 20/125* (2015.11)

(58) Field of Classification Search
CPC ...... C07D 307/50; C08H 8/00; C13K 13/002; C13K 1/02; Y02P 20/125
See application file for complete search history.

(56) References Cited

U.S. PATENT DOCUMENTS

| | | |
|---|---|---|
| 4,018,620 A | 4/1977 | Penque |
| 4,452,640 A | 6/1984 | Chen et al. |
| 8,709,769 B2 | 4/2014 | Weydahl |
| 2010/0058650 A1 | 3/2010 | Gruter et al. |
| 2011/0060148 A1 | 3/2011 | O'Connor et al. |
| 2013/0150595 A1* | 6/2013 | Dumesic ............ C07D 307/48 549/488 |
| 2013/0172582 A1 | 7/2013 | Hutchenson et al. |
| 2013/0252302 A1 | 9/2013 | Pan et al. |
| 2016/0076112 A1 | 3/2016 | Cai et al. |

OTHER PUBLICATIONS

Alcazar-Alay et al., "Study of an Extraction Process as the Pretreatment Step for Sugar Production from Acid Hydrolysis," Food and Public Health, 2015, 5(2), pp. 47-55.
Brennan et al., "Recovery of Sugars from Ionic Liquid Biomass liquor by Solvent Extraction," Bioenergy Research, 2010, 3, pp. 123-133.
Brodeur et al., "Chemical and Physiochemical Pretreatment of Lignocellulosic Biomass: A Review," Enzyme Research, 2011; vol. 2011, Article ID 787532,17 pages.
Carvalheiro et al., "Hemicellulose Biorefineries: A Review on Biomass Pretreatments." Journal of Scientific & Industrial Research, 2008, pp. 849-864.
Di Luccio et al., "Separation of Fructose from a Mixture of Sugars using Supported Liquid Membranes," Journal of Membrane Science, 2000, 174, pp. 217-224.
Dutta et al., "Advances in Conversion of Hemicellulosic Biomass to Furfural and Upgrading Biofuels." Catalysis Science & Technology, 2012, 2, pp. 2025-2036.
Dutta et al., "Direct Conversion of Cellulose and Lignocellulosic Biomass into Chemicals and Biofuel with Metal Chloride Catalysts." Journal of Catalysis, 2012, 288, pp. 8-15.
Grande et al., "Fractionation of Lignocellulosic Biomass using the OrganoCat Process," Green Chemistry, 2015, 17, pp. 3533-3539.
Harris et al., "Two-stage Dilute Sulfuric Add Hydrolysis of Wood: An Investment of Fundamentals," General Technical Report FPL45, 1985, 77 pages.
International Search Report and Written Opinion for International Application No. PCT/US2017/046874 dated Nov. 6, 2017, 8 pages.
Mosier et al., "Features of Promising Technologies for Pretreatment of Lignocellulosic Biomass," Bioresource Technology, 2005, 96, pp. 673-686.
Perlack et al., "Biomass as Feedstock for a Bioenergy and Bioproducts Industry: The Technical Feasibility of Billion-ton Annual Supply," DTIC Document, 2005, 78 pages.
Saha et al., "Advances in 5-hydroxymethylfurfural Production from Biomass in Biphasic Solvents," Green Chemistry, 2014, 16, pp. 24-38.

(Continued)

*Primary Examiner* — John M Mauro
(74) *Attorney, Agent, or Firm* — RatnerPrestia

(57) ABSTRACT

A method of converting a lignocellulosic biomass to monosaccharides, and optionally further converting the monosaccharides to one or both of furfural and HMF, includes contacting the biomass with a reactive liquid phase comprising LiBr, $H_2SO_4$, and water, wherein $H_2SO_4$ preferably constitutes at most 1.0 wt %, more preferably at most 0.5 wt %, and most preferably at most 0.1 wt % of the reactive liquid phase, and water preferably constitutes at most at most 60 wt %, more preferably at most 50 wt %, and most preferably at most 30 wt % of the reactive liquid phase.

17 Claims, 13 Drawing Sheets

(56) References Cited

OTHER PUBLICATIONS

Sluiter et al., "Determination of Sugars, Byproducts, and Degradation Products in Liquid Fraction Process Samples," NREL/TP-510-42618, Jan. 2008, 14 pages.

Springfield et al., "Continuous Ion-Exclusion Chromatography System for Acid/sugar Separation," Separation Science and Technology, May 1999, 34, pp. 1217-1241.

Ahmad et al., "Catalytic and Mechanistic Insights into the Production of Ethyl Levulinate from Biorenewable Feedstocks," Green Chemistry, 2016, 18, pp. 4804-4823.

Alam et al., "Titanium Hydrogenphosphate: An Efficient Dual Acidic Catalyst for 5-hydroxymethylfurfural (HMF) Production," Applied Catalysis A: General, 2014, 486, pp. 42-46.

Bohre et al., "Upgrading Furfurals to Drop-in Biofuels: An Overview," ACS Sustainable Chemistry & Engineering, 2015, 3, pp. 1263-1277.

Cao et al., "Cellulose Hydrolysis using Zinc Chloride as a Solvent and Catalyst," Applied Biochemistry and Biotechnology, 1994, 45/46, pp. 521-530.

Cameiro et al., "Separation of Carbohydrates and Sugar Alcohols from Ionic Liquids using Antisolvents," Separation and Purification Technology, 2014, 132—pp. 496-504.

Choudhary et al., "Xylose isomerization to Xylulose and its Dehydration to Furfural in Aqueous Media," ACS Catalysis, 2011, 1, pp. 1724-1728.

Chun et al., "Influence of Structural Variation in Room-Temperature Ionic Liquids on the Selectivity and Efficiency of Competitive Alkali Metal Salt Extraction by a Crown Ether," Analytical Chemistry, 2001, 73, pp. 3737-3741.

De et al., "Microwave Assisted Conversion Carbohydrates and Biopolymers to 5-hydroxymethylfurfural with Aluminum Chloride Catalyst in Water," Green Chemistry, 2011, 13, pp. 2859-2868.

Delidovich et al., "Cellulose and Hemicellulose Valorisation: An Integrated Challenge of Catalysis and Reaction Engineering," Energy & Environmental Science, 2014, 7, pp. 2803-2830.

Deng et al., "Cellulose Hydrolysis in Acidified LiBr Molten Salt Hydrate Media," Industrial & Engineering Chemistry Research, 2015, 54, pp. 5226-5238.

Duffy et al., "Acidic Nature of Metal Aquo Complexes: Proton-Transfer Equilibria in Concentrated Aqueous Media," Inorganic Chemistry, 1978, 17(10), pp. 2798-2802.

Emons, H., "Structure and Properties of Molten Saft Hydrates," Electrochimica Acta, 1988, 33(9), pp. 1243-1250.

Goswami et al., "One-Pot Conversion of Corn Starch into 5-Hydroxymethylfurfural in Water-[Bmim]Cl/MIBK Biphasic Media," Energy & Fuels, 2016, 30, pp. 8349-8356.

Jeong et al., "Conversion of Red-algae *Gracilaria verrucosa* to Sugars, Levulinic Acid and 5-hydroxymethylfurfural", Bioprocess and Biosystems Engineering, 2015, 38, pp. 207-217.

Lee et al., "An Effective Cellulose-to-Glucose-to-Fructose Conversion Sequence by Using Enzyme Immobilized $Fe_3O_4$-Loaded Mesoporous Silica Nanoparticles as Recyclable Biocatalysts," ChemCatChem, 2013, 5 pages. 2153-2157.

Lee et al., "Integrated, Cascading Enzyme-/Chemocatalytic Cellulose Conversion using Catalysts based on Mesoporous Silica Nanoparticles," ChemSusChem, 2014, 7, pp. 3241-3246.

Nguyen et al., "A Review of Bioretinery Separations for Bioproduct Production via Thermocatalytic Processing," Annual Review of Chemical and Biomolecular Engineering, 2017, 8, pp. 115-137.

Rubin, E., "Genomics of Cellulosic Biofuels," Nature, 2008, vol. 454(14), pp. 841-845.

Sare et al., "Proton Magnetic Resonance Chemical Shifts and the Hydrogen Bond in Concentrated Aqueous Electrolyte Solutions," The Journal of Physical Chemistry, 1973, 77(15), pp. 1869-1876.

Swift et al., "Tandem Lewis Acid/Brønsted Acid-catalyzed Conversion of Carbohydrates to 5-hydroxymethylfurfural using Zeolite Beta," Journal of Catalysis, 2016, 333—pp. 149-161.

Vom Stein et al., "Salt-Assisted Organic-Acid-Catalyzed Depolymerization of Cellulose," Green Chemistry, 2010, 12, pp. 1844-1849.

Xiong et al., "Evaluation of COSMO-SAC Method for the Prediction of the Alcohol-Water Partition Coefficients of the Compounds Encountered in Aqueous Phase Fructose Dehydration," Chemical Engineering Science, 2015, 126, pp. 169-176.

Yuan et al., "Synthesis and Themomechanical Property Study of Novolac Phenol-hydroxymethyl Furfural (PHMF) Resin," RSC Adv., 2014, 4—pp. 31829-31835.

Zhang et al., "Conversion of Xylan, D-Xylose and Lignocellulosic Biomass into Furfural using $AlCl_3$ as Catalyst in Ionic Liquid," Bioresource Technology, 2013, 130, pp. 110-116.

International Preliminary Report on Patentability for International Application PCT/US2017/046874, dated Feb. 19, 2019, 6 pages.

Esteghlalian et al., "Modeling and Optimization of the Dilute-Sulfuric-Acid Pretreatment of Com Stover, Poplar and Switchgrass," Bioresource Technology, 1997, vol. 59, pp, 129-136.

\* cited by examiner

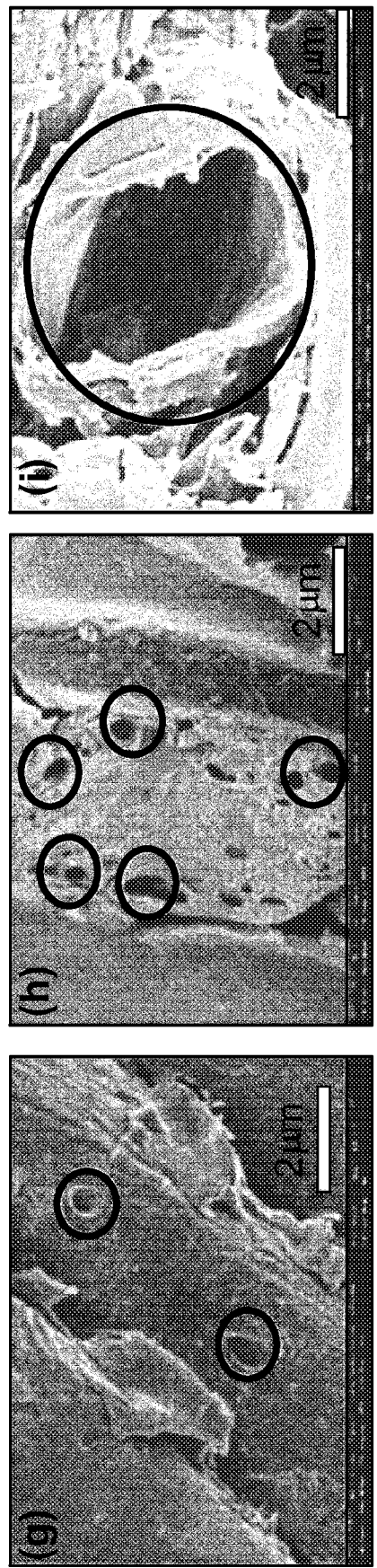

Poplar wood (PW), Soxlet extracted poplar wood (SEPW), and cellulose pulp (CP) depolymerization and saccharification in molten salt hydrate. Yields of soluble and solid products from PW, SEPW and CP are shown in panels (a), (b) and (c), respectively. The corresponding reaction profiles are shown in panels (d), (e) and (f). Respective SEM images with lower magnification are shown in panels (g), (h) and (i). SEM images with higher magnification are in FIG. 4. Reaction conditions: 3.45 wt% PW or SEPW or CP, 59 wt% LiBr, water/salt molar ratio 3.25, 0.05 M $H_2SO_4$, 85°C. SL = soluble lignin. Solids = lignin or lignin with unconverted polysaccharides.

FIG. 1 (Cont.)

HPLC chromatogram of hydrolysate obtained from SEPW depolymerization and saccharification in MSH for 15 min reaction. The yields of CB, Ctr, CTt and CPt are 5.3, 5.3, 7.5 and 5.1 wt%, respectively.

Comparison of glucose and xylose yields at different loadings of SEPW in MSH. Reaction conditions: 59 wt% LiBr, water to salt molar ratio = 3.25, 0.05 M $H_2SO_4$, 85°C.

SEM images of PW (a-c), SEPW (d-f) and CP (g-i) with different magnification. Pores are indexed by circles.

Lignocellulose depolymerization and saccharification results in molten salt hydrate. Reaction conditions: 3.45 wt% biomass, 59 wt% LiBr, water/salt molar ratio 3.25, 0.05 M $H_2SO_4$, 85°C, 1 h reaction time.

The effects of reaction temperatures and AlCl$_3$ concentrations on xylose conversion (a,c) and furfural yields (b,d). Reaction conditions: 1.5 mL xylose hydrolysate containing 30 mg xylose, 4.5 mL EA, The temperature and AlCl$_3$ dependence experiments were performed at fixed AlCl$_3$ (50 mol%) and temperature (120°C), respectively. The yields are on molar basis.

HPLC chromatogram of the MSH phase obtained from dehydration of xylose hydrolysate in biphasic solvent (EA/MSH) showing formation of xylulose as an intermediate.

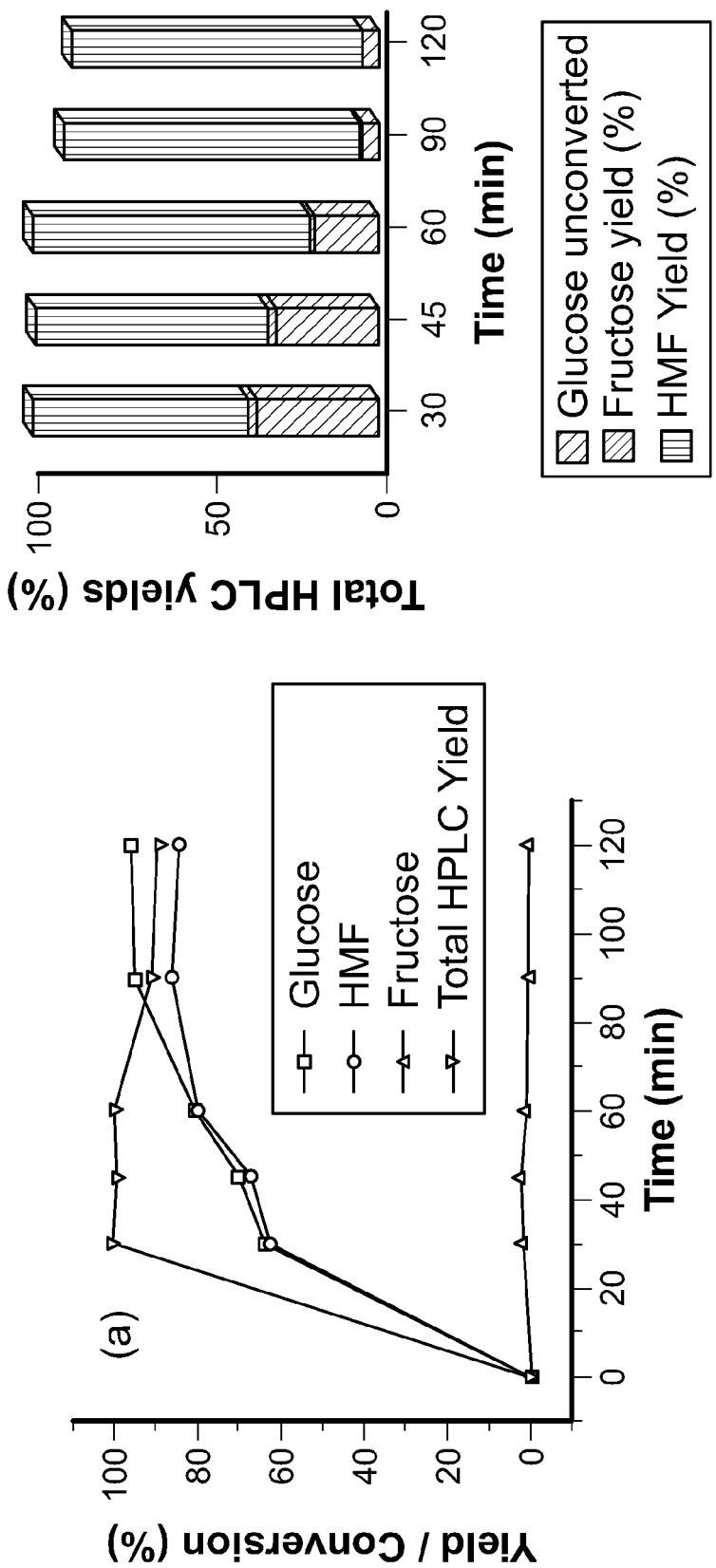

FIG. 8

Dehydration results of glucose hydrolysate (obtained from saccharification of crystalline cellulose in MSH) with AlCl$_3$ in EA/MSH solvent. Reaction conditions: glucose hydrolysate to EA ratio 1:3 (v/v), 120°C, 50 mol% AlCl$_3$. Total HPLC yield in first panel is the combined yields of HMF, fructose and unconverted glucose. Second panel shows a decrease in total HPLC yield over time.

Illustration of integrated saccharification and dehydration processes.

HMF and furfural yields and sugars conversions from dehydration of PW (a), SEPW (b) and CP (c) hydrolysates with AlCl$_3$ (50 mol%) at 120°C Glucose and xylose amounts in 1.5 mL hydrolysates are 30.3 mg and 14 mg for SEPW, 32.1 mg and 4.9 mg for CP. Reaction conditions: hydrolysates to EA ratio 1:3 (v/v), 120°C, 50 mol% AlCl$_3$.

INTEGRATED PROCESS FOR DIRECT SACCHARIFICATION AND DEHYDRATION OF INTACT BIOMASS TO FURFURALS

CROSS REFERENCE TO RELATED APPLICATIONS

This application is a national stage application under 35 U.S.C. § 371 of International Application No. PCT/US2017/046874, filed Aug. 15, 2017, which claims priority to U.S. Provisional Patent Application No. 62/375,991, filed Aug. 17, 2016, the entire contents of which are incorporated herein by reference for all purposes.

STATEMENT REGARDING FEDERALLY SPONSORED RESEARCH

This invention was made with government support under DOE Grant No. DE-SC0001004 awarded by the Department of Energy. The government has certain rights in the invention.

BACKGROUND OF THE INVENTION

Lignocellulosic biomass is an appealing renewable carbon source for fuels and chemicals. Calculation shows that ~33% of fuels and 25% of chemicals demand of the U.S. can be sourced from ~1.3 billion tons of lignocellulosic biomass annually.[1] This outlook has motivated researchers and policy makers towards development of lignocellulose supply chain and conversion technologies to produce fuels, additives and chemicals[2-6] that are commonly obtained from petroleum. However, after a decade of research, many pathways for renewable products have unfavorable process economics, especially when lignocellulosic biomass is considered as a starting feed due to the high processing cost of lignocellulose to $C_5/C_6$ sugars.[7] In traditional practice, recalcitrant lignocellulose, containing cross-linkages of lignin with cellulose and hemicellulose units in the cell microfibril,[8,9] is first pretreated to make polysaccharides amenable for saccharification. The pretreatment employs acid, alkali, ammonia/$CO_2$, or liquid hot water (LHW) under harsh reaction conditions and is energy- and water-intensive, requires complex separation steps, and imparts potentially hazardous effects on the environment.[7] The second step involves saccharification of fractionated polysaccharides to soluble $C_5/C_6$ sugars in an enzymatic process, and is expensive due to high cost of enzyme.

Recently, Inorganic salts based molten salt hydrates (MSHs) have emerged as promising media for saccharification of polysaccharides because of Intrinsic acidity of the media.[10] The MSH consists of a highly concentrated solution of inorganic salt ($C_{salt} \geq 50\%$) that has a water-to-salt molar ratio close to the coordination number of the cation of the salt. The ratio is usually equal to or less than the coordination number of the cation.

The cations of the salts are shielded from anions by one hydration sphere and ion-water interactions predominantly occur in the hydration sphere.[11] As a result, the hydrated cations can polarize water molecules, making their protons acidic in the Brønsted sense. The anions of the salt enhance the acidity by deshielding the protons and increasing their tendency to leave water.[12,13]

MSHs are (1) easy to prepare, (2) environmentally friendly due to their high boiling point and low vapor pressure, and (3) less expensive than common ionic liquids. Because of these advantages, MSHs media have been used for cellulose saccharification.[14-19] However, previous efforts have employed high temperatures (>120° C.) or high acid concentrations (>3 wt %) or long reaction times, which caused degradation of soluble sugars to furanic adducts and humins.[18] A medium for saccharification of crystalline cellulose using LIBr has recently been developed[10]. High yield of soluble sugars (>90%) was achieved in 30 min at 85° C. in which gluco-oligosaccharides were formed as intermediates. However, this and other known processes still suffer overall from insufficient sugar yield and/or high consumption of water and/or energy, and process intensification resulting in fewer processing steps, high yield of sugars, and lower water and energy consumption would be a welcome advance in the industry.

SUMMARY OF THE INVENTION

The invention provides a method of converting a lignocellulosic biomass to monosaccharides, and optionally further converting the monosaccharides to one or both of furfural and HMF, said method comprising contacting the biomass with a reactive liquid phase comprising LiBr, $H_2SO_4$, and water, wherein $H_2SO_4$ preferably constitutes at most 1.0 wt %, more preferably at most 0.5 wt %, and most preferably at most 0.1 wt % of the reactive liquid phase, and water preferably constitutes at most at most 60 wt %, more preferably at most 50 wt %, and most preferably at most 30 wt % of the reactive liquid phase.

The reactive liquid phase may further comprise a Lewis acid, preferably one selected from the group consisting of $CrCl_3$, $SnCl_4$, ZrO(OCl), Sn-Beta, Zr-Beta, Hf-Beta, Sn-MFI, $TiO_2$, and Lewis acidic-carbonaceous materials, for example TI-carbonaceous, and more preferably $AlCl_3$, wherein the Lewis acid is preferably present in an amount of at least 10 mol %, more preferably at least 50 mol %, and most preferably at least 70 mol % relative to total monosaccharides in the liquid phase, and preferably wherein the amount is at most 200 mol % and more preferably at most 150 mol %.

The reactive liquid phase may be in contact with a solvent phase that is immiscible with it, said solvent phase preferably comprising or consisting of one or more organic solvents, more preferably comprising or consisting of one or more solvents selected from the group consisting of methyl isobutyl ketone, methyl tetrahydrofuran, phenolic solvents, dimethyl furan, and m-cresol, and most preferably comprising or consisting of ethyl acetate, wherein the ratio by volume of reactive liquid phase to solvent phase is preferably in a range from 1:10 to 10:1, more preferably from 1:5 to 5:1.

The contacting may be performed at a temperature of at least 25° C. and no higher than 120° C., preferably no higher than 100° C., and more preferably no higher than 90° C.

The method may further include said further converting the monosaccharides to one or both of furfural and HMF, preferably wherein at least 60% of the monosaccharides are converted, more preferably at least 90%, and most preferably at least 99%.

The method may be performed such that the biomass is not pretreated with acid to form polysaccharides prior to said contacting.

The biomass may be plant matter, preferably lignocellulosic biomass, and more preferably intact or extractive-free wood, switch grass, or corn stover.

The yields of glucose and xylose may each individually be at least 50%, or at least 60%, 70%, 80%, 90%, or 95%, based on the glucan and xylan content of the biomass, respectively.

The yields of HMF and furfural may each individually be at least 50%, or at least 60%, 70%, 75%, or 80%, based on the amount of monomeric and oligomeric glucose and xylose produced by the contacting, respectively.

The yields of HMF and furfural may each individually be at least 50%, or at least 60%, 70%, 75%, or 80%, based on the glucan and xylan content of the biomass, respectively.

The viscosity of the reactive liquid phase may be at least 2 mPa s, or at least 3, 4, or 5 mPa s.

BRIEF DESCRIPTION OF THE DRAWINGS

FIG. 8 shows results of glucose hydrolysate dehydration performed according to the invention.

DETAILED DESCRIPTION OF THE INVENTION

As used herein, references to percent values are on a weight basis unless otherwise specified or made apparent by the context. Biomass is considered "intact" if it has not undergone chemical processing to separate lignin from carbohydrates.

The inventors now disclose that LiBr is effective for one-step depolymerization and saccharification of untreated lignocellulose to soluble sugars with high yields at low temperature. The inventors elucidate the effects of lignocellulose extractives and lignin on the rates of depolymerization using microscopic techniques. Techno-economic analysis shows that the inventive processes are highly competitive compared with traditional two-step processes. The inventors further disclose an efficient method of converting the soluble sugars to furfurals.

Conversion of Lignocellulosic Biomass to Sugars

Figure 1:
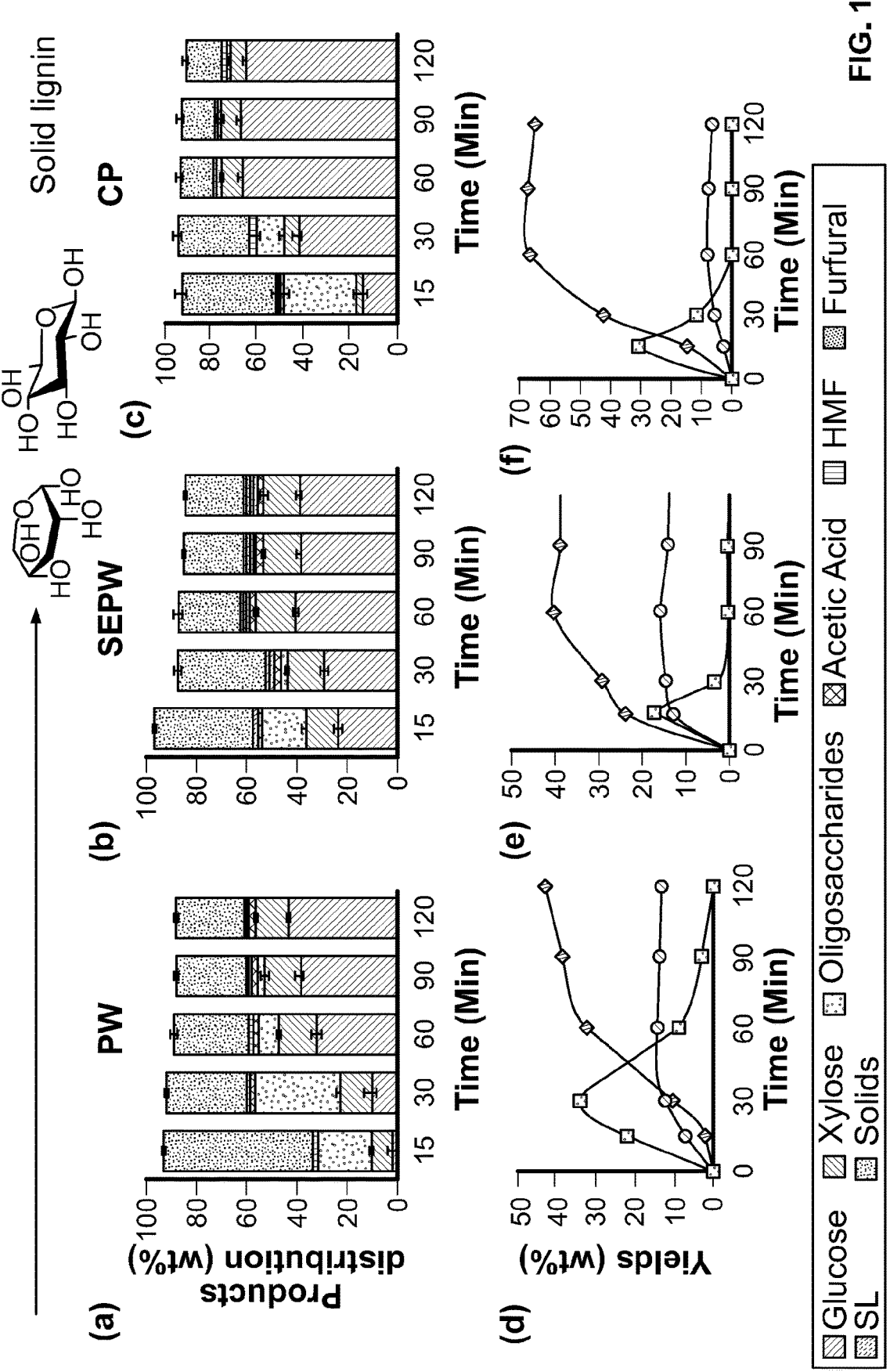
FIG. 1 shows depolymerization results according to the invention for several types of biomass.
Figure 2:
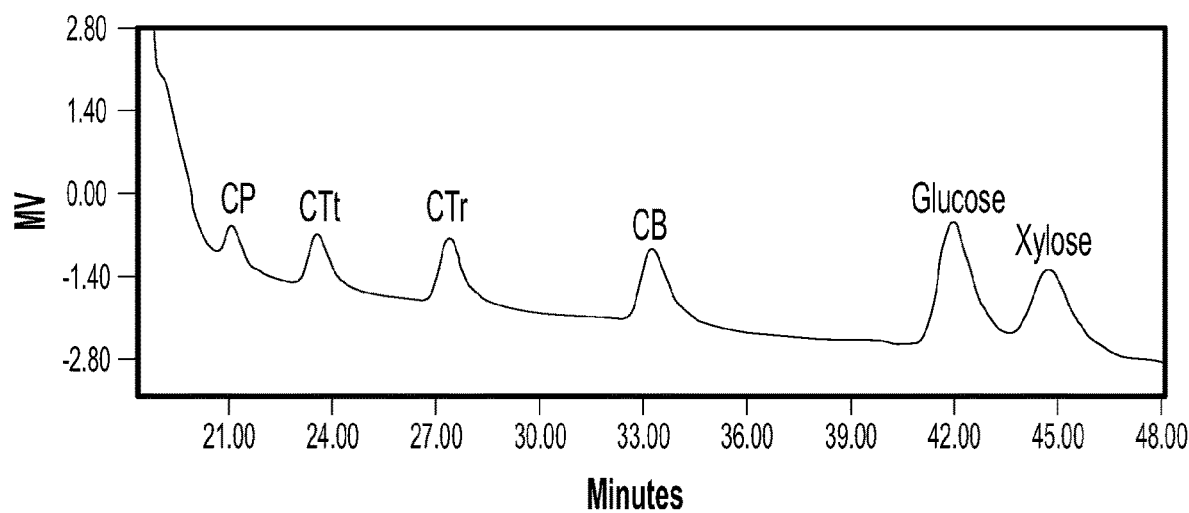
FIG. 2 is a chromatogram showing species produced by depolymerization and saccharification of Soxlet extracted poplar wood (SEPW) according to the invention.
Figure 3:
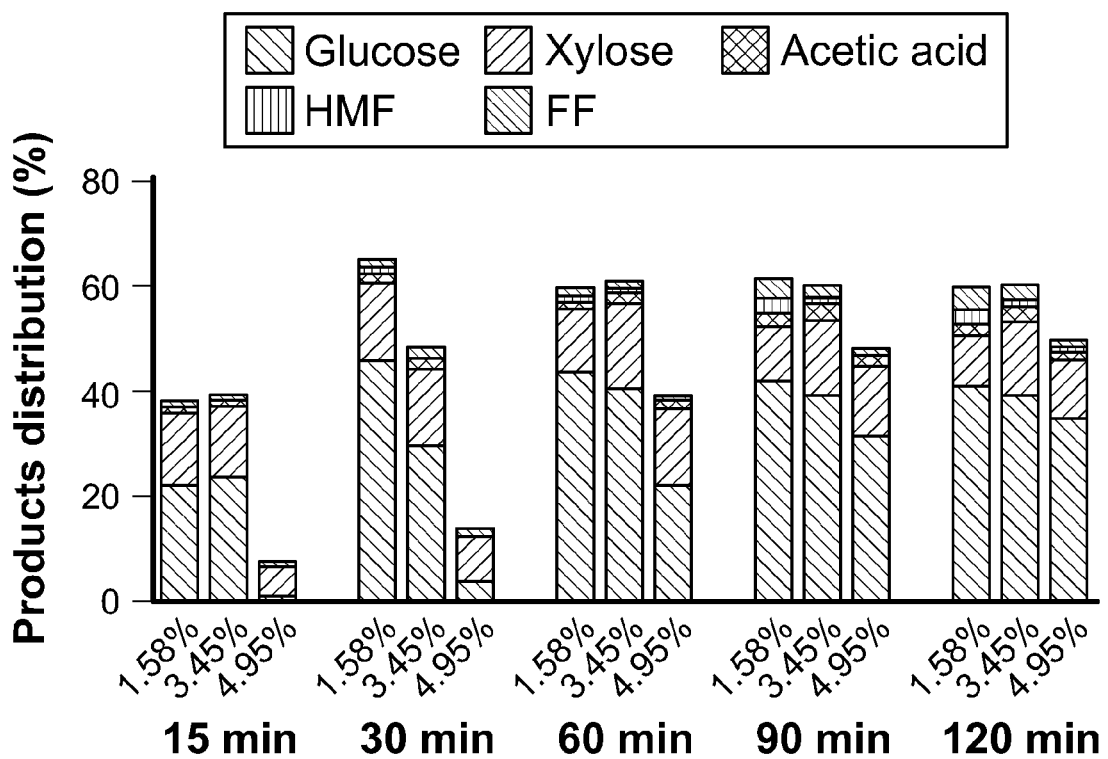
FIG. 3 shows the effect of SEPW loading on glucose and xylose yields produced according to the invention.

First the Inventors examined the effectiveness of the LiBr-MSH for depolymerization of intact poplar wood (PW) and Soxlet extracted poplar wood (SEPW). At optimal reaction conditions developed for cellulose saccharification, SEPW depolymerization in MSH progresses through formation of gluco-oligosaccharides. Characteristic HPLC peaks for xylo-oligosaccharides, including xylobiose, disappeared quickly (5 min), suggesting saccharification of biomass hemicellulose takes place rapidly upon its dissolution. Most of the xylose was formed within 15 min, while about 50% glucose remained unsaccharified in gluco-oligosaccharides or undepolymerized biomass (FIG. 1, panel b; Table 1). Detected gluco-oligosaccharides were cellobiose (CB), cellotriose (CTr), cellotetrose (CTt) and cellopentose (CPt) (FIG. 2). A small amount of acetic acid (AA) was formed from acetate-xylan, which is present in PW.[20] The recovered solid (40 wt %) contained unconverted polysaccharides and lignin. The yield of glucose Increased upon depolymerization and saccharification of remaining polysaccharides in SEPW and gluco-oligosaccharides. About 90% of theoretical glucan and xylan were saccharified in 1 h from SEPW (Table 1). Lignin was formed as a solid with a small fraction in soluble form (soluble lignin; SL). Monosaccharide yield did not improve upon continuing the reaction for another 1 h; rather a slight dehydration of sugars to HMF and furfural is observed. FIG. 1 panel e presents the reaction profile showing SEPW depolymerization and gluco-oligosaccharides saccharification. These results, demonstrating high yields of soluble sugars in one step without the need for a pretreatment step or high consumption of water and acid additive, represent a significant process Intensification for low-temperature conversion of lignocellulose processing to soluble sugars, currently a hurdle in cellulosic biorefineries. Lower SEPW loading (1.58 wt %) resulted in a slightly higher glucose and similar xylose yields (FIG. 3). Higher SEPW loading (4.95 wt %) might have caused insufficient stirring of the slurry using a magnetic stir bar, hence yielding a little less glucose (6 wt %) than that observed at 3.4 wt % SEPW loading.

TABLE 1

Yield of glucose and xylose from depolymerization and saccharification of different biomass in MSH.

| Biomass samples | Time (min) | Yield (wt %) based on dry weight of biomass | | Yield (wt %) based on theoretical glucan and xylan in biomass | |
|---|---|---|---|---|---|
| | | Glucose | Xylose | Glucose | Xylose |
| PW | 15 | 2.2 | 7.8 | 4.9 | 43.4 |
| | 30 | 10.6 | 12.5 | 23.3 | 69.6 |
| | 60 | 32.2 | 14.5 | 71.0 | 80.6 |
| | 90 | 38.7 | 14.1 | 85.4 | 78.2 |
| | 120 | 42.9 | 13.4 | 94.7 | 75 |
| SEPW | 15 | 23.9 | 13.0 | 52.8 | 74.6 |
| | 30 | 29.6 | 14.3 | 65.4 | 82.4 |
| | 60 | 40.5 | 15.8 | 89.3 | 90.7 |
| | 90 | 39.1 | 14.2 | 86.3 | 81.5 |
| | 120 | 39.3 | 13.6 | 86.7 | 78.1 |
| CP | 15 | 15.1 | 3.4 | 21.2 | 37.6 |
| | 30 | 42.7 | 6.5 | 59.9 | 72.0 |
| | 60 | 67.0 | 8.1 | 94.0 | 89.6 |
| | 90 | 67.8 | 7.8 | 95.2 | 86.6 |
| | 120 | 65.3 | 6.9 | 91.7 | 76.5 |
| Pine[a] | 60 | 39.4 | 21 | 89.5 | 84 |
| Douglas Fir[a] | 60 | 41.0 | 21.2 | 85.4 | 85 |
| Alder[a] | 60 | 36.6 | 19.4 | 85.1 | 78 |
| Switch Grass[a] | 60 | 30.4 | 24.5 | 70.6 | 82 |
| Corn Stover[a] | 60 | 14.0 | 19.6 | 33.3 | 63.2 |

Reaction conditions: 3.45 wt % biomass, 59 wt % LiBr, water/salt molar ratio 3.25, 0.05M $H_2SO_4$, 85° C.,
[a]1 h reaction time.

To assess the effect of biomass extractives on depolymerization, the inventors used intact PW without the removal of biomass extractives. Under comparable reaction conditions, PW depolymerization is very slow in the beginning of the reaction (FIG. 1, panel a). Unlike SEPW, the reaction with intact PW gives negligible glucose in 15 min, with the majority of depolymerized cellulose remaining in the form of gluco-oligosaccharides. The concentration of total gluco-oligosaccharides, of which CPt is 11 wt %, increased to 33 wt % at 0.5 h. Higher Mw soluble oligosaccharides (DP>5) might have been formed during depolymerization; however the inventors could not qualitatively and quantitatively determine these species by the inventors' HPLC method due to their high Mw. Further saccharification of oligomers formed an amount of glucose similar that obtained from SEPW, but required a longer reaction time (2 h). Comparison of reaction profiles (FIG. 1, panels d and e) reveals that the rates of PW depolymerization to gluco-oligosaccharides and their further saccharification to glucose are significantly slower than those for SEPW.

The inventors further evaluated the effect of lignin on the depolymerization, using cellulose-pulp (CP) obtained from an organic acid-assisted pretreatment of SEPW in a biphasic solvent consisting of aqueous oxalic acid and MeTHF, detailed in the Examples. This process removed 39 wt % of total PW lignin (10 wt % on the basis of dry biomass) and 38 wt % of total hemicellulose (7 wt % on the basis of dry biomass) Including acetate-xylan, in the form of xylose and AA from SEPW, while cellulose content was untouched. The resultant CP, containing significantly less lignin and hemicellulose than did SEPW or PW, was subjected to depolymerization in MSH. FIG. 1 panels c and f show faster conversion of CP, achieving 31 wt % gluco-oligosaccharides within 15 min and maximum 67 wt % glucose on the basis of dry CP weight (95% based on theoretical glucan) in 1 h. The remaining solid (mostly lignin) and detected soluble products accounts for the mass balance. The results show that partial removal of lignin and hemicellulose from SEPW by pretreatment enhances the rates of CP depolymerization and gluco-oligosaccharides saccharification.

Figure 4:
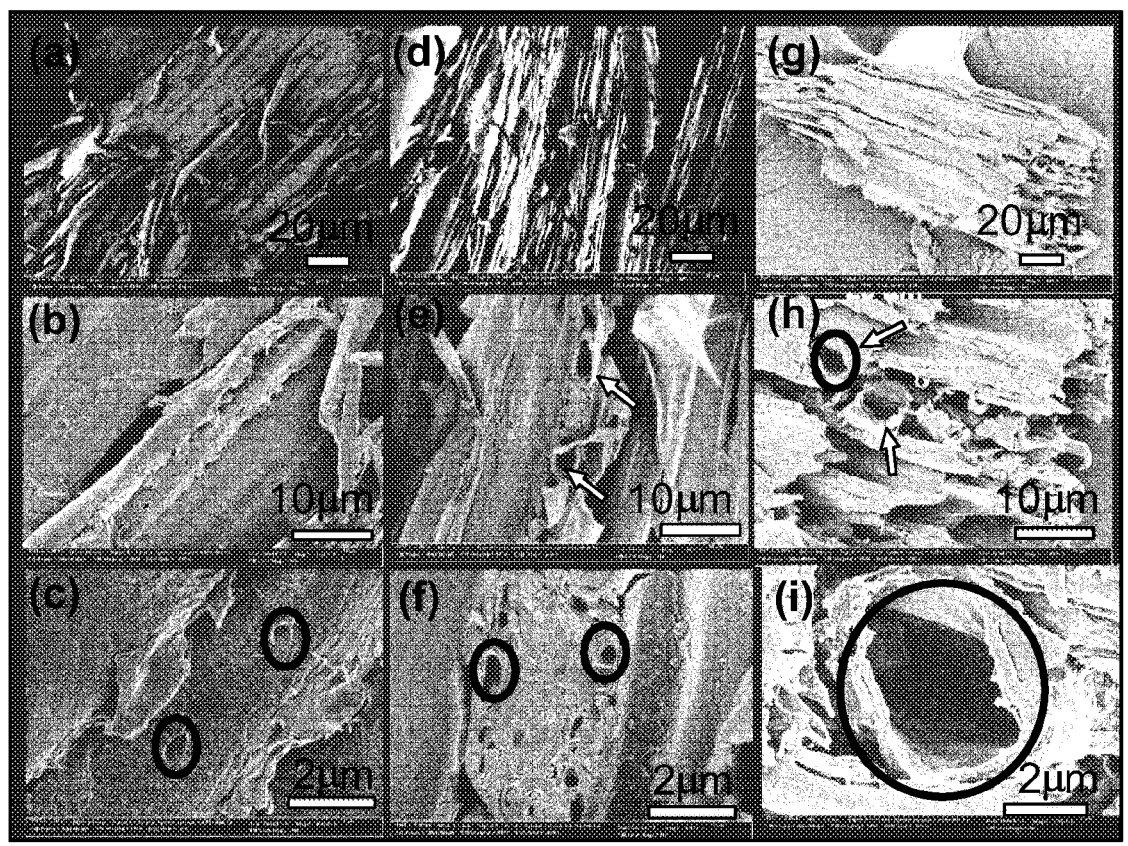
FIG. 4 shows scanning electron microscope images of poplar wood and SEPW.

To understand the differences in depolymerizaton, the inventors studied morphological features of PW, SEPW and CP by Scanning Electron Microscope (SEM) (FIGS. 1 and 4). The higher magnified SEM images (FIG. 1, panel g for PW and h for SEPW) show the presence of a more porous structure in the SEPW sample due to the removal of extractives during Soxlet extraction. The porous structure and higher surface area of pores allows greater accessibility and better interactions of the SEPW fibers with the salt solution, resulting in faster depolymerization than for PW. This result agrees with a previous report demonstrating improved yields of saccharified monosaccharides from Soxlet extracted palm pressed fiber containing pores.[21] Similarly, CP exhibited faster conversion due to processing of samples with much larger pores (FIG. 1, panel i). Importantly, partial lignin removal upfront from SEPW also makes CP less recalcitrant, enabling faster conversion.

Figure 5:
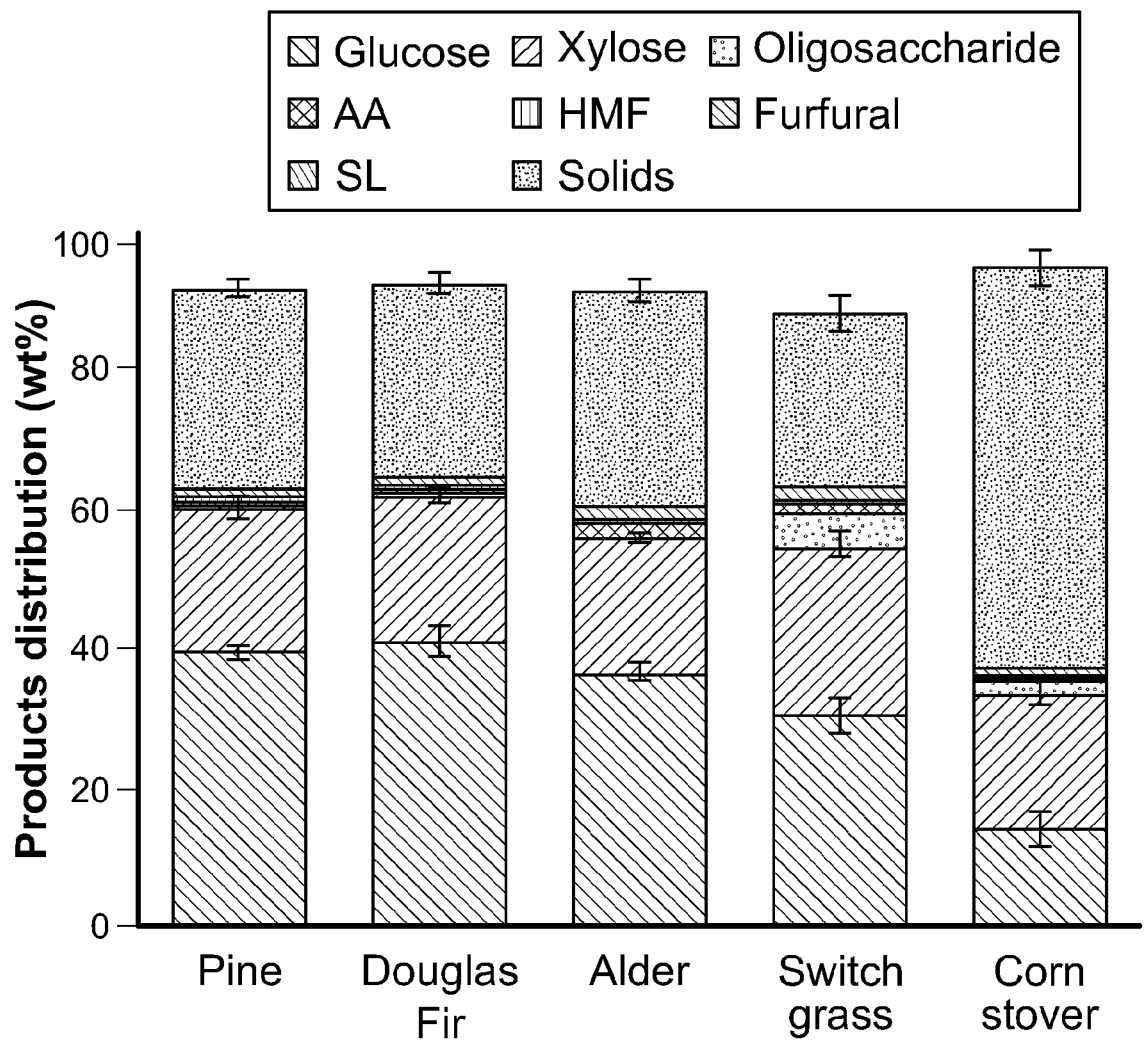
FIG. 5 shows depolymerization and saccharification results for several types of biomass according to the invention.

To evaluate the potential of the MSH for depolymerization of other lignocellulose, extractive-free pine, switch grass, corn stover, Douglas Fir and alder biomass of similar particle size (1 mm) was used (FIG. 5, Table 2). Pine and Douglas Fir samples yielded comparable amounts of glucose as SEPW. Alder biomass yielded a little less monosaccharides due to its high lignin content (33 wt %). Switch grass and corn stover, especially corn stover, produced significantly less glucose, possibly due to neutralization of acidity of the MSH solution by the basic metals of corn stover containing high amount of ash.[22]

TABLE 2

Compositional analysis data for biomass feeds

| | Compositional analysis data in wt % | | | | |
|---|---|---|---|---|---|
| Components | Pine | Switch Grass | Corn Stover | Douglas Fir | Alder |
| Glucan | 44 | 41 | 42 | 48 | 43 |
| Xylan | 25 | 30 | 31 | 25 | 25 |
| Lignin | 28 | 20 | 15 | 29 | 33 |
| Ash | 1.5 | 1 | 4 | 1 | 0.2 |
| Extractive | 7 | 6 | 12 | 3 | 2 |

Conversion of Sugars to Furfurals

The inventors now also address the separation of soluble sugars from MSH hydrolysate, which is necessary for recycling MSH. Salt extraction by crown ethers[23] and sugars separation by boronic acid complexation-decomplexation,[24] antisolvents,[25] liquid membranes[26] and ion exclusion chromatography[27] have previously been attempted. However, these methods are either slow or expensive and are impractical for large scale separation. The inventors now disclose conversion of sugars to furfurals (HMF and furfural) in a biphasic system, an approach that allows concurrent reactive extraction of furfurals into an extraction solvent and recycling of the reactive phase (MSH). This results in process intensification that addresses both sugars separation and furfurals production in an integrated manner.

Conversion of sugars to furfurals progresses via isomerization and dehydration reactions, and requires Lewis and Brønsted acid sites.[28] The Lewis acid isomerizes $C_6/C_5$ aldoses to the corresponding ketoses, while the Brønsted acid dehydrates the ketoses to HMF/furfural. The inventors previously reported that homogeneous metal salts are effective catalysts for the conversion of glucose and xylose to HMF and furfural, respectively, and that the reaction was accelerated with addition of Brønsted acids.[29, 30] In the present invention, the inventors used $AlCl_3$ and a biphasic solvent to convert glucose/xylose in hydrolysates to HMF/furfural. First, the inventors screened several organic extracting solvents of high partition coefficients predicted by COSMO-SAC[31] and optimized the reaction conditions for glucose and xylose dehydration separately in MSH hydrolysates. Usually inorganic salts in the aqueous phase improve partitioning of furfurals into the organic phase due to the salting out effect.[3, 32] Interestingly MSH behaves negatively with most organic solvents in partitioning HMF and furfural. For example, HMF partitioning into methyl isobutyl ketone (MIBK) enhanced in the presence of 30 wt % NaCl in water in a MIBK/water biphasic system (partition coefficient=1.2).[32] It is noteworthy that the inventors' experiment using pure HMF showed a very low partition coefficient for HMF (0.5) in MIBK/MSH (1:3 (v/v)). Similarly, the COSMO-SAC model predicted a high partition coefficient for HMF (33.8) in m-cresol/water, a finding which was experimentally validated.[32] However, in the m-cresol/MSH system, HMF forms a condensation product with m-cresol, which agrees with a previous report[33]. This results in an erroneous partition coefficient for HMF. Control experiments reveal the formation of a similar condensation product between HMF and MIBK in MSH, resulting in about four-fold mass loss of added HMF. Furanic solvents (tetrahydrofuran (THF) and 2-methyl tetrahydrofuran (2-MeTHF)), which form separate phases with pure water or NaCl saturated water, are miscible with MSH. Screening experiments identified ethyl acetate (EA) as the best solvent among those tested for extracting HMF and furfural from MSH hydrolysate.

Figure 6:
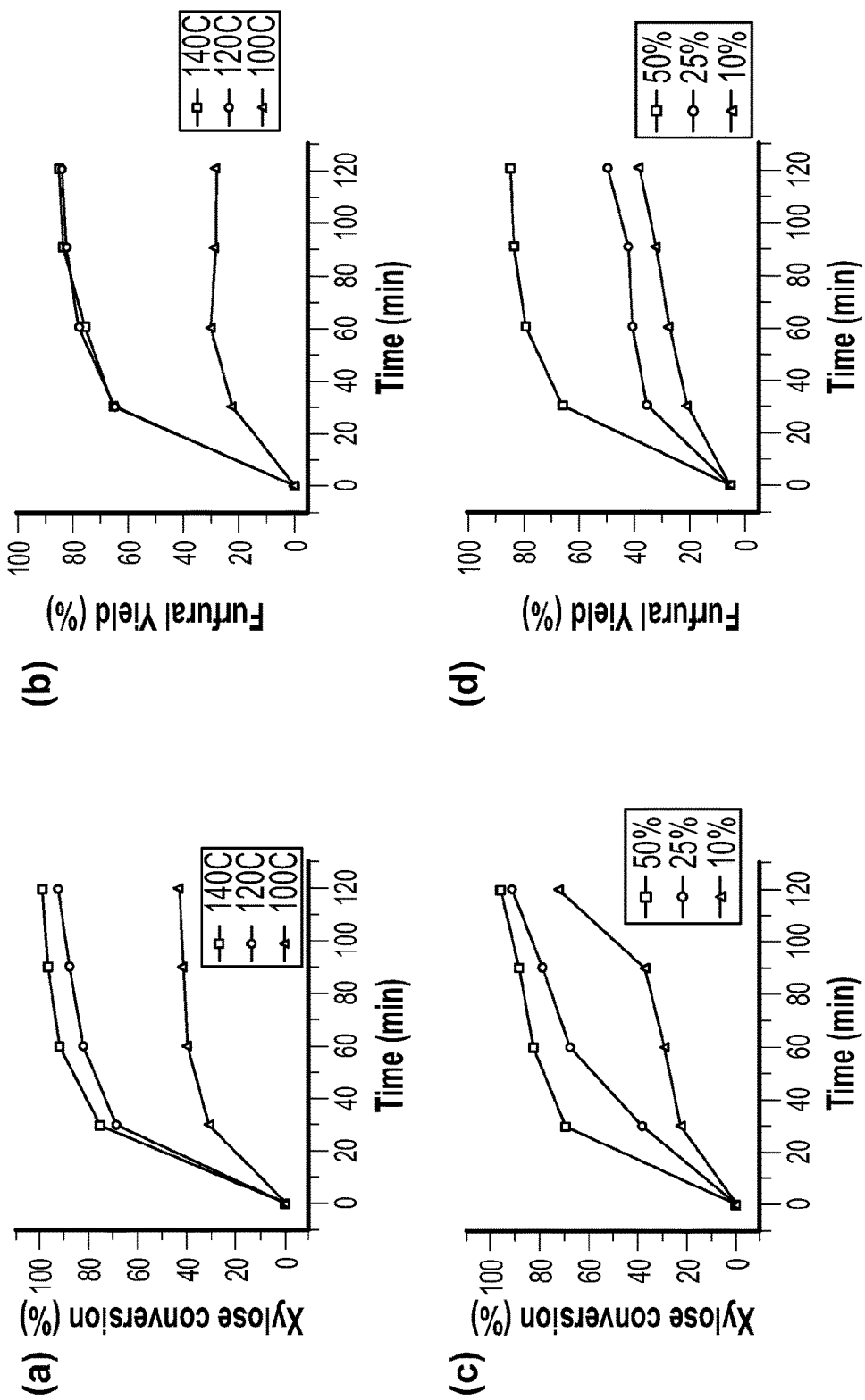
FIG. 6 shows the effects of reaction conditions on xylose conversion and furfural yields using conversion methods according to the invention.
Figure 7:
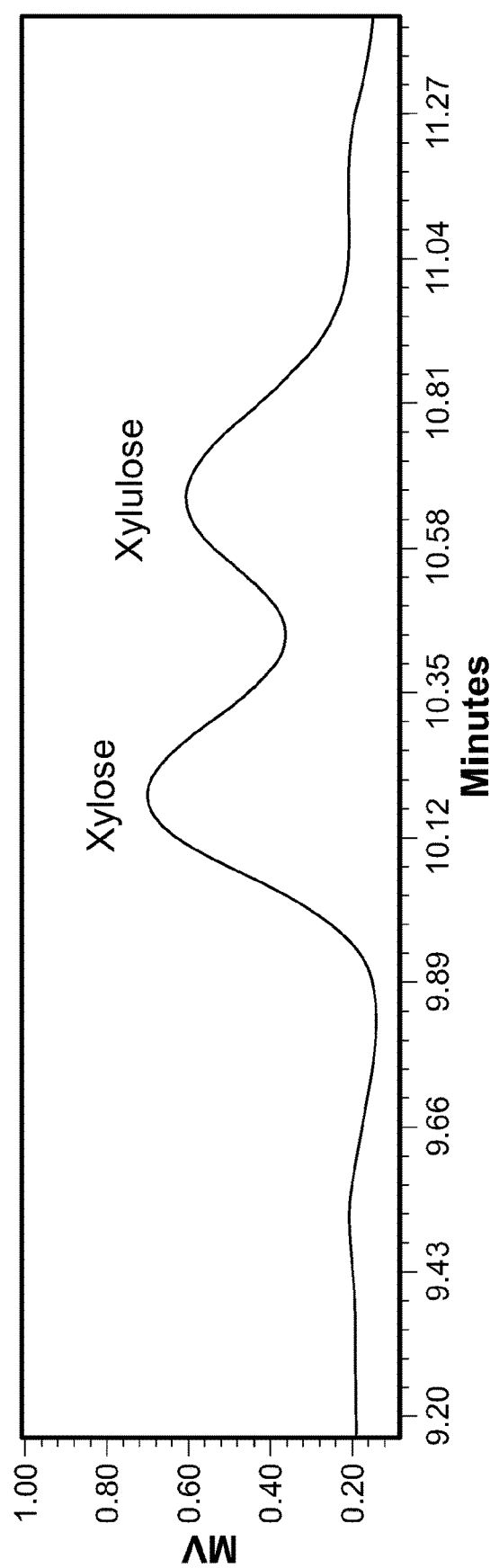
FIG. 7 is a chromatogram of the molten salt hydrate reactive liquid phase using a biphasic process according to the invention.

The inventors optimized the reaction conditions for sugar dehydration in EA/MSH by varying the reaction temperature (100-140° C.) and $AlCl_3$ (10-50 mol % on the basis of sugar amount). Xylose was used as a model sugar for optimization of dehydration conditions. The results show maximum 84 mol % furfural yield from xylose hydrolysate with 50 mol % $AlCl_3$ at 120° C. for 2 h (FIG. 6). The Inventors have previously established that the reaction progresses via xylulose Intermediate (FIG. 7).[34] Xylose conversion is nearly quantitative (99%); thus, some carbon mass loss occurs during dehydration. The solution turned brownish during the reaction, Indicating oligomerization of furfural (potentially with xylose/xylulose) to form humins.

Figure 9:
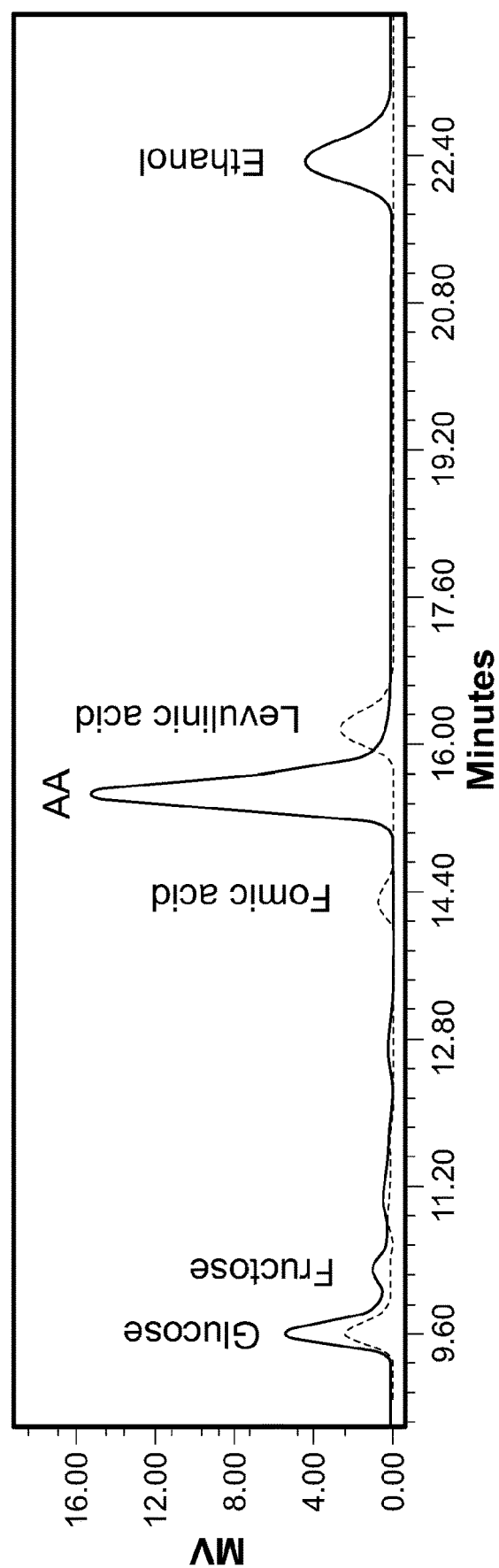
FIG. 9 shows chromatograms of products obtained by monophasic and biphasic dehydration of glucose hydrolysate according to the invention.

Under comparable reaction conditions, the conversion of glucose hydrolysate containing 33 mg glucose, obtained from cellulose saccharification in MSH, achieved 80 mol % HMF yield in 1 h in EA/MSH biphasic solvent. After 2 h the yield improved to a maximum of 85 mol %, but the total HPLC yield, representing the combined yield of HMF, fructose, and unconverted glucose, decreased (FIG. 8). This indicates some carbon loss to form of humins with increased reaction time. HMF rehydration forms levulinic acid (LA) in an MSH monophasic system, but LA formation was not evident in a biphasic reaction system by HPLC analysis, as seen in FIG. 9. The product solution obtained from dehydration of glucose hydrolysate in MSH (shorter trace) shows formation of levulinic acid and formic acid. However, the chromatogram of the MSH phase obtained from dehydration of glucose hydrolysate in EA/MSH biphasic solvent (taller trace) shows no peaks for levulinic acid or formic acid. This suggests that HMF rehydration takes place in monophasic MSH but not in biphasic solvent. Acetic acid (AA) and ethanol in the biphasic reaction are thought to have formed by hydrolysis of EA.

Figure 10:
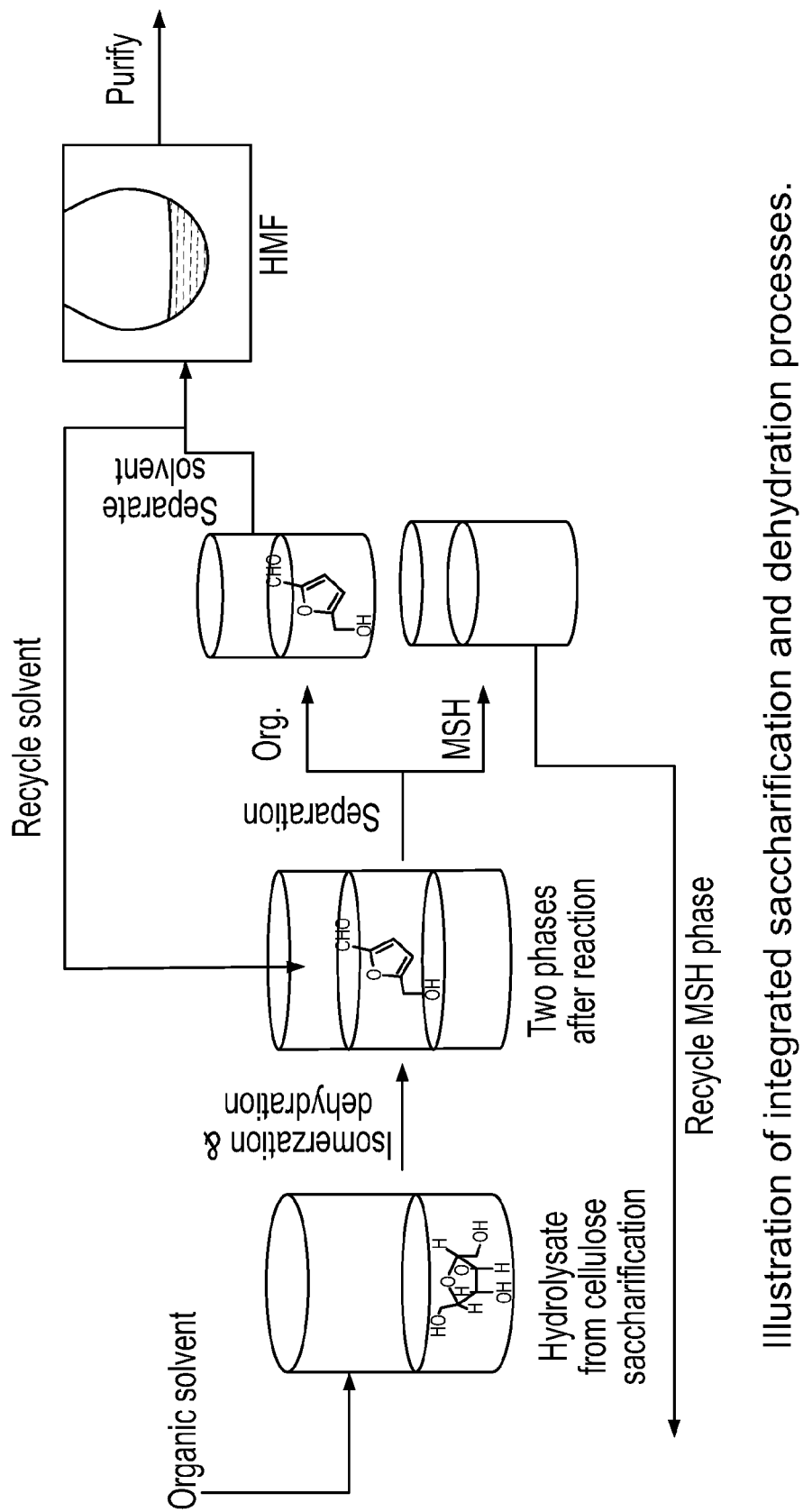
FIG. 10 is a schematic view of integrated saccharification and dehydration processes according to the invention.

The recovered MSH phase containing LiBr and Lewis acidic $Al^{3+}$, upon decantation of the organic phase containing HMF (FIG. 10), was reused in the $2^{nd}$ cycle in which cellulose saccharification and glucose dehydration occurred in the same reactor. The reused MSH solution yielded slightly less HMF (78 mol %). A slight yield loss in the $2^{nd}$ cycle could be due to a loss of Li-salt (0.04%) into the organic phase as observed from ICP-MS analysis of the crude HMF. The inventors evaluated the effect of MSH on sugars dehydration by comparing the inventors' results with the literature results reported in non-MSH systems. Maximum reported HMF and furfural yields in biphasic solvents containing non-MSH as an aqueous phase are 68 mol %[35] and 84 mol %[36] at 140° C. and 170° C., respectively. This comparison suggests that there may be a cooperative effect between Lewis and Brønsted acids in MSH that, possibly along with the high viscosity of the MSH medium, may account for the enhanced HMF yield in the inventors' reactions.

Figure 11:
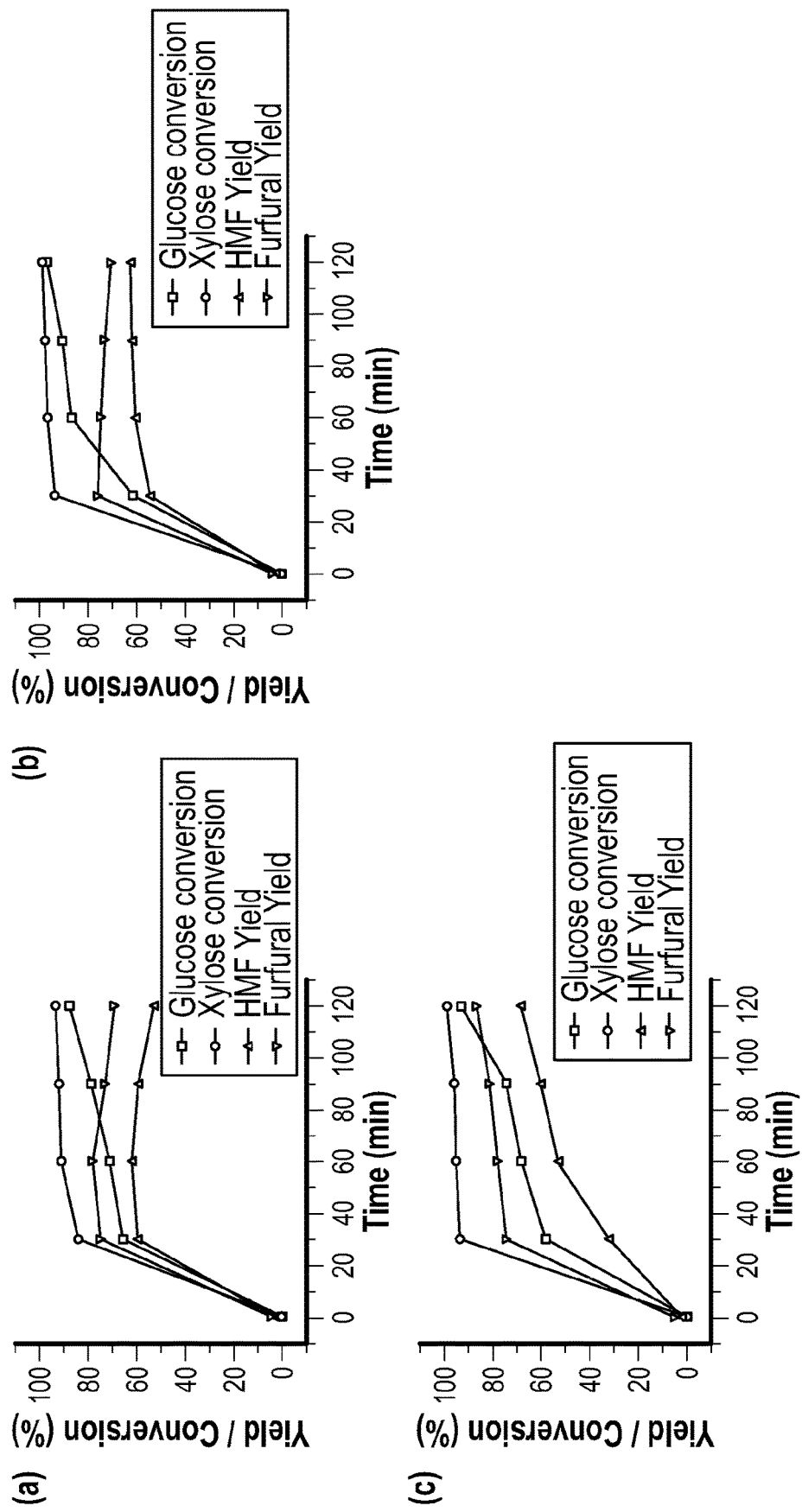
FIG. 11 shows HMF and furfural yields and sugars conversions from dehydration of several types of biomass with $AlCl_3$ according to the invention.

Biomass hydrolysates from SEPW, PW and CP depolymerization and saccharification were similarly dehydrated in EA/MSH at 120° C. for 2 h. FIG. 11 compares HMF and furfural formation from each hydrolysate. SEPW hydrolysate yields 60 mol % HMF within 1 h, which increased slightly in 2 h. Furfural formation occurs faster than HMF, achieving 78 mol % yield within 0.5 h and maintains similar concentration for 2 h. This suggests that HMF and furfural products are stable in the organic phase and side products (LA, humins, FA) may form in the MSH phase, accounting for carbon mass loss. HMF and furfural formation profiles from PW hydrolysate followed similar trends in the beginning of the reaction; however HMF and furfural degradation occurred after 1 h and the solution became dark colored, suggesting that biomass extractives in the solution might accelerate oligomerization of furfurals with sugars resulting in dark colored humins formation. CP hydrolysate gave higher HMF (68 mol %) and furfural (87 mol %) yields, possibly due to partial removal of lignin upfront from the substrate and hence minimization of soluble lignin that could inhibit dehydration. However, the exact reason is unclear. Interestingly, glucose and xylose conversion profiles for all the three hydrolysates are comparable. This indicates that the nature and extent of impurities in the hydrolysates may affect HMF and furfural degradation and product selectivity.

Techno-economic analysis for HMF production, using the inventors' observed glucose yield from the MSH process and HMF recovery, was performed using Aspen Economic analyzer V8.6. Annual biomass processing capacity of the production plant is assumed as 400,000 metric tons. Minimum price, which is defined as the minimum production cost of a product at the Net Present Value (NPV) of zero, of HMF from the MSH process is compared with two other processes in which commercially relevant dilute acid (DA) and concentrated acid (CA) saccharification technologies are used for processing biomass to sugars in two-steps. In the DA process, biomass is first pretreated with 1.6 wt % $H_2SO_4$ at 170° C. for 12 min.[37] The resulting solid is treated with 0.8 wt % acid in the second step at 230° C. for 40 s. The yield of glucose is 57%. The CA process[38] involves depolymerization of biomass to oligosaccharides with a mixture of $H_2SO_4$ and $H_3PO_4$ (2:1 w/w) at 50° C. in the first step, followed by saccharification of oligosaccharides to sugars (glucose and xylose) with 90% yield in the second step at 140° C. Biomass loading for the DA and CA processes are assumed as 25 wt % and 40 wt % as per the reported values, whereas biomass loading in the MSH process is assumed as 10 wt %. The sensitivity analysis shows lower minimum price of HMF at higher biomass loading (vide infra). The reaction conditions for dehydration of sugars in hydrolysates obtained from all the processes are assumed similar. Furfural and lignin are formed as co-products, except in the DA process in which xylose is separated in the first step and hence furfural yield is low. These co-products are assumed as by-products with no value for estimation of HMF minimum price.

Figure 12:
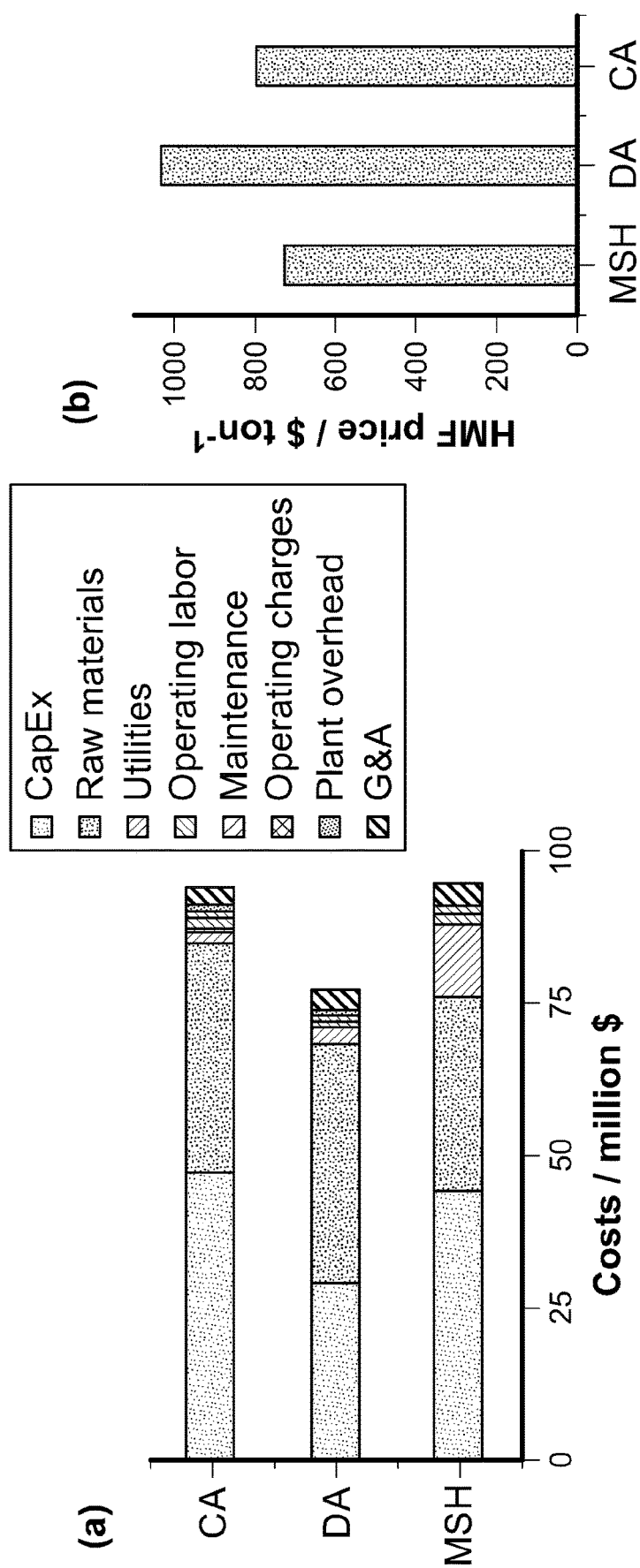
FIG. 12 compares fixed (CapEx), breakdown operating costs and HMF production cost for the MSH process of this invention with those of two prior art processes.

Aspen simulation predicts annual production volume of HMF from the MSH, DA and CA processes as 81072, 51925 and 70488 metric tons with HMF purity of 98%, 96% and 96%, respectively. While the yield of HMF from glucose dehydration is assumed to be the same for the three processes, total HMF production from each process is controlled by glucose yield in biomass depolymerization and saccharification step. FIG. 12 compares fixed (CapEx) and breakdown operating costs for the three processes. CapEx of the CA process is maximum because special materials requirement for handling concentrated acid. CapEx of the MSH process is slightly lower than the CA process. The high organic solvent requirement for HMF extraction and associated separation of the solvent by distillation makes overall utility costs of the MSH process high. Interestingly, total costs of the DA process is lower than the other two processes; however, minimum price of HMF from the MSH process ($729/metric ton) is lower than that of the DA ($1032/metric ton) and CA ($795/ton) processes. Sensitivity analysis shows a 34% decrease in the minimum price of HMF from the MSH process at biomass loading similar to the CA process (40 wt % loading). Thus, the MSH process has significant cost advantages for HMF production due to its single stage conversion technology as well as higher glucose yield.

EXAMPLES

Materials

Lithium bromide, 5 M sulfuric acid, aluminium chloride hexahydrate, ethyl acetate, m-cresol, oxalic acid, ethanol, 2-methyl tetrahydrofuran (MeTHF) and HPLC standards (xylose, glucose, acetic acid, formic acid, levulinic acid, 5-hydroxymethylfurfural, furfural) were purchased from Sigma-Aldrich. Gluco- and xylo-oligosaccharides with degree of polymerization (DP) of 2-6 with >95% purity were purchased from Megazymes. All chemicals were used as received. Unless otherwise mentioned, deionized water (Millipore model Direct-Q3 UV R) was used for preparation of all solutions. Syringe filter discs (Nylon, 0.2 μm) for filtration of solutions for HPLC analysis were purchased from Fisher Scientific. Beech wood xylan containing 6.5% moisture was purchased from TCI America. Poplar, Alder, Pine, Switch grass, Douglas Fir and corn stover biomass were purchased from Forest Concepts, LLC. Particle size of hardwood sample is approximately 1 mm (l×w×h). Compositional analysis using NREL procedure[40] suggests that poplar wood sample contains 45.3% glucan, 18% xylan, 25.5% lignin, 0.8% ash and 5% extractives (weight basis). The remaining 5% could be others (Advanced Hardwood Biofuels Northwest 2013a, http://crf.sandia.gov/thermo-chemical-integration-key-to-improving-the-efficiency-of-blo-ethanol-production). Compositional analysis data of pine, switch grass, corn stover, Douglas Fir and alder biomass samples are given in Table 2. As per NREL procedure, these data have ±5% uncertainty.

Soxlet Extraction

Biomass samples containing variable amount of moisture were washed consecutively with ethanol followed by water each for 4 hr using a Soxlet extraction setup. After Soxlet extraction, washed samples were dried at 30° C. for overnight and moisture content was measured using a moisture analyzer.

Fractionation of Poplar Wood

Fractionation of Soxlet extracted poplar wood (SEPW) to cellulose enriched pulp (referred hereto as cellulose-pulp; CP) was carried out by OrganoCat pretreatment method in a biphasic system.[39] In this method, SEPW (4 g) was treated with 40 mL of 0.1 M aqueous solution of oxalic acid and 40 mL MeTHF at 140° C. for 4 h in a stainless steel Parr reactor. Upon completion of reaction for the set time, the reactor was cooled down to room temperature and the mixture was allowed to settle. The organic phase containing soluble lignin was separated by decantation. The aqueous phase was filtered to separate solid cellulose pulp and the filtrate was analyzed by HPLC to quantify the yield of soluble sugars, mainly xylose. Dry weight of the pulp was 2.56 g (73 wt % based on dry weight of SEPW). Compositional analysis by NREL procedure shows that the pulp after partial removal of hemicelluloses and lignin contains 70.2 wt % glucan, 9 wt % xylan and 15.3 wt % lignin. Thus, 39 wt % of total lignin of poplar wood was removed during fractionation. HPLC analysis shows that the aqueous solution contains 50 wt % xylan and 33 wt % acetic acid and 1.3% glucose from SEPW. These calculations are based on xylan, acetate form of xylan and glucan amount in SEPW.

Depolymerization and Saccharification

Saccharification of xylan, cellulose, untreated poplar wood, Soxlet extracted biomass samples and cellulose-pulp was conducted in high pressure glass vials. The vial was loaded with calculated amount of LiBr and 0.05 M aqueous sulfuric acid in amounts calculated to maintain a water:LiBr molar ratio of 3.25:1. Upon dissolving LiBr, the calculated amount of substrate (crystalline cellulose, xylan or biomass) to keep substrate concentrations up to 6 wt % was added into the vial and the mixture was vortexed for about 30 sec. The vial was sealed with an Al-crimp cap and placed in a preheated heating block to start depolymerization at 85° C. (or other desired temperature) with continuous stirring using a magnetic bar. Upon completion of reaction for the set time, the vial was removed from the heating block and quenched in an ice bath. The hydrolysate was diluted 1:10 with deionized water and filtered for HPLC analysis.

Dehydration of Sugars to Furfurals $C_6/C_5$ sugars in the hydrolysates, obtained from crystalline cellulose, xylan or biomass, were dehydrated to furfurals (HMF or furfural or both) in a biphasic system. Typically, 1 mL hydrolysate was mixed with amounts of $AlCl_3 \cdot 6H_2O$ varying from 10 mol % to 50 mol % relative to total sugars in the hydrolysates, along with an organic extracting solvent (ethyl acetate, EA) in a high pressure glass vial. The ratios of the hydrolysate (reactive phase) to organic solvent were varied in the range of 1-3 (v/v). Upon addition of a small magnetic bar into the vial for stirring, the vial was sealed with an Al-crimp cap and placed in a preheated stainless steel heating block preset at desired temperature. After completion of the reaction for the set time, the vial was removed from the heating block and quenched in an ice bath. The solution was allowed to settle to ensure separation of the two phases. The organic phase containing furfurals was decanted in a collection flask and the aqueous phase containing MSH was washed two times with EA (2×5 mL) to extract remaining HMF or furfural or both. Both EA and MSH phases were filtered for analysis by HPLC. The MSH phase was diluted 1:10 with deionized water before analysis.

Recycling MSH

Recyclability of the MSH was evaluated for the saccharification of pure cellulose in MSH at a LiBr to water molar ratio of 3.25 (1.46 g LiBr, 1 mL 0.05 M acid, 39.5 mg cellulose, total volume 1.5 mL). After saccharification of cellulose at 85° C. for 30 min, the hydrolysate containing soluble glucose was subjected to dehydrate in MSH-EA (1:3 (v/v)) biphasic system at 120° C. for 1 h using $AlCl_3$ (50 mol % with respect to the molar amount of glucose, 32.7 mg glucose in 1.5 mL, 22 mg $AlCl_3 \cdot 6H_2O$). After decantation of the organic phase containing HMF and washing the aqueous phase twice with EA, the recovered solution containing MSH and Al-species was filtered through a syringe filter and reused in the $2^{nd}$ cycle. The yields of glucose and HMF after the hydrolysis and the dehydration steps were quantified by HPLC. The unconverted amount of glucose that remained in the hydrolysate after the $1^{st}$ cycle of dehydration was accounted during addition of cellulose in the $2^{nd}$ cycle. EA was added to adjust the ratio of EA to MSH phase to 3 (v/v) and the mixture was heated at 120° C. for 1 h. Cellulose saccharification and glucose dehydration takes place simultaneously in the $2^{nd}$ cycle as the recovered aqueous phase from the $1^{st}$ cycle contains both MSH and $AlCl_3$. Upon completion of the $2^{nd}$ cycle, the organic and aqueous phases were worked out by following the same procedure discussed above and the reactive phase was reused.

Selection of Organic Solvents for HMF and Furfural Extraction

The inventors determined partition coefficient (R) values of different organic solvents for selection of the best organic solvent for extraction of furfurals from the MSH phase. These experiments were performed in a jacketed glass reactor equipped with a thermostatted bath to set desired temperature of the reaction mass. MSH solution was prepared by mixing 8.22 g LIBr in 10 mL $H_2O$ (water to LiBr molar ratio is 3.25). HMF (0.91 g, 5 wt %) was added to the MSH solution and dissolved by stirring the solution. To this, calculated amount of EA was added to adjust the ratios of organic and aqueous phase of 1 and 3 (v/v) in order to evaluate the effect of volume of the extracting solvent on HMF partitioning. The mixture was stirred at 60° C. for 1 h and settled overnight to ensure complete phase separation. HMF concentrations in both phases were quantified by HPLC upon dilution. All experiments were conducted in triplicate.

Analysis and Quantification of Various Products

Sugar hydrolysates and the aqueous and organic phases from sugar hydrolysates dehydration reactions were diluted 10-fold, unless otherwise mentioned, and analyzed on a Waters HPLC instrument (model e2695) equipped with a photodiode array (PDA) detector (Waters 2998) as well as a refractive index (RI) detector (Waters 2414). Three HPLC columns of following specifications were used for analysis of different sugar and furfurals products at different operating conditions. (1) A Bio-Rad Aminex HPX-87H (7.8×300 mm, 9 μm) column operating at column oven temperature of 55° C., an aqueous solution of $H_2SO_4$ (0.005 M) as a mobile phase at flow rate of 0.6 mL/min was used for detection and quantification of glucose (9.52 min), xylose (10.14 min), fructose (10.26 min), xylulose (10.41), formic acid (14.23 min), acetic acid (15.48 min), Levulinic acid (16.16 min) 5-hydroxymethylfurfural (30.22 min) and furfural (45.58 min) using a PDA detector (254 nm). The number in parenthesis refers to the retention time of the species. (2) An Agilent Hiplex Na (7.7×300 mm, 10 μm) column operating at column oven temperature of 85° C. and deionized water a mobile phase at flow rate of 0.2 mL/min was used for analysis of oligosaccharides using an RI detector. This column and HPLC operating conditions detected gluco- and xylo-oligosaccharides of DP (degree of polymerization) up to 6. Retention times of for detected oligosaccharides are given in Table 3. (3) An Agilent Zorbax SB C18 (4.6×250 mm, 5 μm) column operating at column oven temperature of 25° C. and acetonitrile-water mixture (1:1 v/v) as a mobile phase at flow rate of 0.3 mL/min was used for analysis of HMF in the organic phase from sugar hydrolysates dehydration experiments using a PDA detector (254 nm). The characteristic peaks for organic products and sugar monosaccharides and oligosaccharides were identified from the retention times of the authentic samples. Each peak was integrated, and the actual concentrations of each product were calculated from their respective pre-calibrated plots of peak areas vs. concentrations. The yields of various products ($C_6/C_5$ monosaccharides, oligosaccharides, HMF, furfural and other soluble products from cellulose/xylan saccharification and biomass (PW, SEPW, CP depolymerization and saccharification) were calculated by following equations.

$C_6$ monosaccharides and oligosaccharides yields from cellulose saccharification $$\text{Yield (wt \%)}_{C6mono/oligosaccharides} = \frac{\text{Yields in mg measured from } HPLC}{\text{Cellulose in mg} \times F1} \times 100 \quad (1)$$

where F1 is Mw of mono- or oligosaccharides/162

$C_5$ monosaccharides and oligosaccharides yields from xylan saccharification $$\text{Yield (wt \%)}_{C5mono/oligosaccharides} = \frac{\text{Yields in mg measured from } HPLC}{\text{Xylan in mg} \times F2} \times 100 \quad (2)$$

where F2 is w of mono- or oligosaccharides/132

$C_6/C_5$ monosaccharides, oligosaccharides HMF, furfural yields from PW or SEPW or CP depolymerization and saccharification $$\text{Yield (wt \%)} = \frac{\text{Yields in mg measured from } HPLC}{\text{Dry wt. of } PW \text{ or } SEPW \text{ or } CP} \times 100 \quad (3)$$

C6/C5 monosaccharides yields on the basis of theoretical glucan and xylan amounts in PW or SEPW or CP samples $$\text{Yield (wt \%)} = \frac{\text{Yields in mg measured from } HPLC}{\text{Theoretical glucan or xylan amounts in } PW \text{ or } SEPW \text{ or } CP} \times 100 \quad (4)$$

Furfurals (HMF, furfural) yield from dehydration of glucose and xylose in cellulose or xylan or biomass hydrolysates $$\text{Yield (mol \%)}_{HMF,Ff,fructose,xylulose,FA,LA} = \frac{\text{Yield in mol measured from } HPLC}{\text{Initial glucose or xylose in hydrolysates(in mol)}} \times 100 \quad (5)$$

Where FA, LA and Ff are formic acid, levulinic acid and furfural

HMF Partition coefficient was calculated using the following equation $$\text{Partition coefficient}_{HMF} = \frac{HMF_{Organic\ phase}}{HMF_{aqueous\ phase}} \quad (6)$$

TABLE 3

Retention times of various xylo- and gluco-oligosaccharides.

| Oligosaccharides | RT (min) |
|---|---|
| Xylobiose | 37.55 |
| Xylotriose | 32.26 |
| Xylotetraose | 28.23 |
| Xylopentaose | 22.86 |
| Xylohexaose | 25.18 |
| Cellobiose | 33.36 |
| Cellotriose | 27.43 |
| Cellotetraose | 23.62 |
| Cellopentaose | 20.92 |
| Cellohexaose | 19.23 |

Scanning Electron Microscopy (SEM)

SEM analysis of biomass samples was performed on an Auriga 60 microscope (Carl Zeiss NTS GmbH, Germany) equipped with a Schottky Field Emission Gun (FEG). All samples were deposited on adhesive carbon tape and sputtered by a DESK IV sputter unit (Denton Vacuum Inc. NJ, USA) equipped with Au/Pd target.

In summary, the inventors present a one-pot approach to process a variety of lignocellulose to soluble sugars using an inorganic salt solution. This process using significantly less water than the enzymatic or acidic saccharification processes and enables nearly quantitative yield of soluble sugars at 85° C. in short reaction time. Lignin is separated as a solid. Extractive-free and partially lignin-removed biomass samples produce sugars at faster rates due to greater accessibility and better interactions of their porous fibers with the salt solution. Biomass extractives also caused faster degradation of furans, formed from dehydration of sugars, resulting in undesired humins and carbon loss. The process integration enables sugars separation in the form of furans via reactive extraction and recycling of the salt solution. Techno-economic analysis shows significant cost advantages of the inventors' process when compared with commercially relevant dilute and concentrated acid processes.

Although the invention is illustrated and described herein with reference to specific embodiments, the Invention is not Intended to be limited to the details shown. Rather, various modifications may be made in the details within the scope and range of equivalents of the claims without departing from the invention.

REFERENCES

[1] R. D. Perlack, L. L. Wright, A. F. Turhollow, R. L. Graham, B. J. Stokes, D. C. Erbach in Biomass as feedstock for a bioenergy and bioproducts industry: the technical feasibility of a billion-ton annual supply, DTIC Document, 2005.

[2] S. Dutta, S. De, B. Saha, M. I. Alam. *Catalysis Science & Technology*, 2012, 2, 2025-2036.

[3] B. Saha, M. M. Abu-Omar *Green Chemistry*. 2014, 16, 24-38.

[4] A. Bohre, S. Dutta, B. Saha, M. M. Abu-Omar. *Acs Sustainable Chemistry & Engineering*, 2015, 3, 1263-1277.

[5] (a) E. Ahmad, M. I. Alam, K. Pant, M. A. Haider. *Green Chemistry*, 2016, 18, 4804-4823; (b) Y-C. Lee, S. Dutta, K. C.-W. Wu. *ChemSusChem*, 2014, 7, 3241-3246; (c) Y-C. Lee, C-T. Chen, Y-T. Chiu, K. C.-W. Wu. *ChemCatChem*, 2013, 5, 2153-2157; (d) M. I. Alam, S. De, B. Singh, B. Saha, M. M. Abu-Omar. *Applied Catalysis A: General*, 2014, 486, 42-48; (d) G-T. Jeong, C. H. Ra, Y-K. Hong, J. K. Kim, I-S. Kong, S-K. Kim, D-H. Park. Bioprocess and Biosystems Engineering, 2015, 38, 207-217.

[6] I. Delidovich, K. Leonhard, R. Palkovits. *Energy & Environmental Science*, 2014, 7, 2803-2830.

[7] G. Brodeur, E. Yau, K. Badal, J. Collier, K. Ramachandran, S. Ramakrishnan. *Enzyme research*, 2011, 2011.

[8] N. Mosier, C. Wyman, B. Dale, R. Elander, Y. Lee, M. Holtzapple, M. Ladisch. *Bioresource technology*, 2005, 96, 673-686.

[9] E. M. Rubin *Nature*. 2008, 454, 841-845.

[10] W. Deng, J. R. Kennedy, G. Tsilomelekis, W. Zheng, V. Nikolakis. *Industrial & Engineering Chemistry Research*, 2015, 54, 5226-5236.

[11] H.-H. Emons. *Electrochimica Acta*, 1988, 33, 1243-1250.

[12] E. Sare, C. Moynihan, C. Angell. *The Journal of Physical Chemistry*, 1973, 77, 1869-1876.

[13] J. Duffy. M. Ingram *Inorganic Chemistry*, 1978, 17, 2798-2802.

[14] T. vom Stein, P. Grande, F. Sibilla, U. Commandeur, R. Fischer, W. Leitner, P. D. de Maria. *Green Chemistry*, 2010, 12, 1844-1849.

[15] N. J. Cao, Q. Xu, C. S. Chen, C. S. Gong, L. F. Chen. *Applied Biochemistry and Biotechnology*, 1994, 45-6, 521-530.

[16] R. A. Penque. In Method of hydrolyzing cellulose to monosaccharides, U.S. Pat. No. 4,018,620 A, 1977.

[17] R. M. D. A. Paul O'Connor, Sjoerd Daamen, Jacob A. Moulijn, Michiel Makkee. In Process for converting polysaccharides in an inorganic molten salt hydrate, US patent 0060148 A1, 2011.

[18] C.-M. Y. Li Fu Chen. In Quantitative hydrolysis of cellulose to glucose using zinc chloride, U.S. Pat. No. 4,452,640 A, 1984.

[19] L. S. Xuejun Pan. In Saccharification of lignocellulosic biomass, US patent 0252302 A1, 2013.

[20] F. Carvalheiro, L. C. Duarte, F. M. Girio. *Journal of Scientific & Industrial Research*, 2008, 849-864.

[21] F. P. C.-T. Sylvia C. Alcázar-Alay, Diego T. Santos, M. Angela A. Meireles. *Food and Public Health*, 2015, 5, 47-55.

[22] A. Esteghlalian, A. G. Hashimoto, J. J. Fenske, M. H. Penner. *Bioresource Technology*, 1997, 59, 129-136.

[23] S. Chun, S. V. Dzyuba, R. A. Bartsch. *Analytical Chemistry*, 2001, 73, 3737-3741.

[24] T. C. Brennan, S. Datta, H. W. Blanch, B. A. Simmons, B. M. Holmes. *BioEnergy Research*, 2010, 3, 123-133.

[25] A. P. Carneiro, O. Rodríguez, E. A. Macedo. *Separation and Purification Technology*, 2014, 132, 496-504.

[26] M. Di Luccio, B. Smith, T. Kida, C. Borges, T. Alves. *Journal of Membrane Science*, 2000, 174, 217-224.

[27] R. Springfield, R. Hester. *Separation science and technology*, 1999, 34, 1217-1241.

[28] T. D. Swift, H. Nguyen, Z. Erdman, J. S. Kruger, V. Nikolakis, D. G. Vlachos. *Journal of Catalysis*, 2016, 333, 149-161.

[29] S. De, S. Dutta, B. Saha. *Green Chemistry*, 2011, 13, 2859-2868.

[30] S. Dutta, S. De, M. I. Alam, M. M. Abu-Omar, B. Saha. *Journal of Catalysis*, 2012, 288, 8-15.

[31] R. Xiong, J. Miller, M. LeÓn, V. Nikolakis, S. I. Sandler. *Chemical Engineering Science*, 2015, 126, 169-176.

[32] H. Nguyen, R. F. DeJaco, N. Mittal, J. I. Siepmann, M. Tsapatsis, M. A. Snyder, W. Fan, B. Saha, D. G. Vlachos. *Annual Review of Chemical and Biomolecular Engineering*. 2017, 8, DOI: 10.1146/annurev-chembioeng-060816-101303.

[33] Z. Yuan, Y. Zhang, C. C. Xu. *RSC Adv.*, 2014, 4, 31829.

[34] V. Choudhary, A. B. Pinar, S. I. Sandler, D. G. Vlachos, R. F. Lobo. *ACS Catalysis*, 2011, 1, 1724-1728.

[35] S. Roy Goswami, A. Mukherjee, M.-J. Dumont, V. Raghavan. *Energy & Fuels*, 2016, 30, 8349-8356.

[36] L. Zhang, H. Yu, P. Wang, H. Dong, X. Peng. *Bioresource technology*, 2013, 130, 110-116.

[37] J. F. Harris, A. Baker, T. Jeffries, J. Minor, R. C. Pettersen. *General technical report FPL*. 1985, 45.

[38] K. R. Weydahl. In Process for the production of alcohol, U.S. Pat. No. 8,709,769, 2014.

[39] P. M. Grande, J. Viell, N. Theyssen, W. Marquardt, P. Dominguez de Maria, W. Leitner. *Green Chemistry*, 2015, 17, 3533-3539.

[40] A. H. Sluiter, B.; Ruiz, R.; Scarlata, C.; Suiter, J.; Templeton, D.; Crocker, D *NREL*. 2008, TP-510-42618.

What is claimed:

1. An integrated one-pot two-step method of converting an intact lignocellulosic biomass to C5 and C6 monosaccharides, and further converting the C5 and C6 monosaccharides to furfural and HMF, said method comprising:
   a first step of contacting the intact lignocellulosic biomass with a reactive liquid phase comprising LiBr, $H_2SO_4$, and water to convert the biomass to C5 and C6 monosaccharides, and
   a second step of contacting the reactive liquid phase with a Lewis acid and an organic solvent immiscible with the reactive liquid phase to form a biphasic system, wherein a conversion of C5 and C6 monosaccharides to furfural and HMF occurs in the reactive liquid phase with concurrent extraction of furfural and HMF from the reactive liquid phase to the organic solvent phase,
   wherein a ratio by volume of the reactive liquid phase to the organic solvent phase is in a range from 1:10 to 10:1,
   wherein $H_2SO_4$ constitutes at most 1.0 wt % of the reactive liquid phase, and water constitutes at most 60 wt % of the reactive liquid phase, and
   wherein the reactive liquid phase is a LiBr-molten salt hydrate phase.

2. The integrated method according to claim 1, wherein the Lewis acid is selected from the group consisting of $AlCl_3$, $CrCl_3$, $SnCl_4$, $ZrO(OCl)$, Sn-Beta, Zr-Beta, Hf-Beta, Sn-MFI, $TiO_2$, and Lewis acidic-carbonaceous materials, and wherein the Lewis acid is present in an amount of at least 10 mol % and at most 200 mol % relative to total C5 and C6 monosaccharides in the reactive liquid phase.

3. The integrated method according to claim 1, wherein the organic solvent phase comprises ethyl acetate and wherein the ratio by volume of the reactive liquid phase to the solvent phase is in a range from 1:5 to 5:1.

4. The integrated method according to claim 3, wherein the step of contacting the reactive liquid phase with the organic solvent phase is performed at a temperature of at least 25° C. and no higher than 140° C.

5. The integrated method according to claim 1, wherein at least 60% of each of the C5 and C6 monosaccharides are converted to furfural and HMF respectively.

6. The integrated method according to claim 1, wherein the C5 and C6 monosaccharides comprise glucose and xylose and wherein the yields of glucose and xylose in the reactive liquid phase are each individually at least 50%, based on the glucan and xylan content of the biomass, respectively.

7. The integrated method according to claim 1, wherein the yields of HMF and furfural in the organic solvent phase are each individually at least 50%, based on the amount of C5 and C6 monosaccharides produced in the reactive liquid phase, respectively.

8. The integrated method according to claim 1, wherein the viscosity of the reactive liquid phase is at least 2 mPa·s.

9. The integrated method according to claim 1 further comprising the steps of separating the organic solvent phase from the biphasic system and reusing the reactive MSH liquid phase containing LiBr, $H_2SO_4$, water, and the Lewis acid by:
   contacting the used reactive MSH liquid phase with another batch of intact lignocellulosic biomass, and
   adding the organic solvent comprising ethyl acetate to the used reactive MSH liquid phase such that a ratio by volume of the used reactive MSH liquid phase to the organic solvent phase is in a range from a range from 1:10 to 10:1.

10. An integrated one-pot two-step method of converting a lignocellulosic biomass to C5 and C6 monosaccharides, and further converting the C5 and C6 monosaccharides to furfural and HMF, said method comprising:
    a first step of contacting the lignocellulosic biomass with a reactive molten salt hydrates (MSH) liquid phase comprising LiBr, $H_2SO_4$, and water to convert the biomass to C5 and C6 monosaccharides, and
    a second step of contacting the reactive MSH liquid phase with a Lewis acid and an organic solvent immiscible with the reactive MSH liquid phase to form a biphasic system, wherein a conversion of C5 and C6 monosaccharides to furfural and HMF occurs in the reactive MSH liquid phase with concurrent extraction of furfural and HMF from the reactive MSH liquid phase to the organic solvent phase,
    wherein the organic phase comprises ethyl acetate,
    wherein a ratio by volume of the reactive MSH liquid phase to the organic solvent phase is in a range from 1:10 to 10:1, and
    wherein $H_2SO_4$ constitutes at most 1.0 wt % of the reactive MSH liquid phase, and water constitutes at most 60 wt % of the reactive MSH liquid phase.

11. The integrated method according to claim 10, wherein the Lewis acid is selected from the group consisting of $AlCl_3$, $CrCl_3$, $SnCl_4$, $ZrO(OCl)$, Sn-Beta, Zr-Beta, Hf-Beta, Sn-MFI, $TiO_2$, and Lewis acidic-carbonaceous materials and wherein the Lewis acid constitutes at least 10 mol % and at most 200 mol % relative to total monosaccharides in the reactive liquid phase.

12. The integrated method according to claim 10, wherein the lignocellulosic biomass is not pretreated prior to said contacting.

13. The integrated method according to claim 10, wherein the lignocellulosic biomass comprises intact or extractive-free and partially lignin-removed biomass; or intact or extractive-free wood, switch grass, corn stover, pine, douglas fir, alder, partially lignin-removed cellulose pulp or cellulose.

14. The integrated method according to claim 10, wherein the yields of HMF and furfural in the organic solvent phase are each individually at least 60%, based on the amount of C5 and C6 monosaccharides produced in the reactive phase, respectively.

15. The integrated method according to claim 10 further comprising the steps of separating the solvent phase from the biphasic system and reusing the reactive MSH liquid phase containing LiBr, $H_2SO_4$, water, and the Lewis acid by:
    contacting the reactive MSH liquid phase with another batch of lignocellulosic biomass, and
    adding an organic solvent comprising ethyl acetate to the used reactive MSH liquid phase such that a ratio by volume of the used reactive MSH liquid phase to the organic solvent phase is in a range from a range from 1:10 to 10:1.

16. The integrated method according to claim 10, wherein the step of contacting the reactive MSH liquid phase with the organic solvent phase is performed at a temperature of at least 25° C. and no higher than 140° C.

17. The integrated method according to claim 10, wherein side products of the conversion of C5 and C6 monosaccharides to furfural and HMF remain in the reactive MSH liquid phase, the side products comprising levulinic acid, humins and formic acid.

* * * * *